United States Patent
Agresta et al.

(10) Patent No.: US 11,234,976 B2
(45) Date of Patent: Feb. 1, 2022

(54) METHODS OF USING PYRUVATE KINASE ACTIVATORS

(71) Applicant: Agios Pharmaceuticals, Inc., Cambridge, MA (US)

(72) Inventors: Samuel V. Agresta, Lexington, MA (US); Yue Chen, Quincy, MA (US); Marvin B. Cohen, Newtown, PA (US); Lenny Dang, Boston, MA (US); Charles Kung, Arlington, MA (US); Elizabeth A. Merica, Boston, MA (US); Bruce A. Silver, Dunkirk, MD (US); Hua Yang, Acton, MA (US)

(73) Assignee: Agios Pharmaceuticals, Inc., Cambridge, MA (US)

( * ) Notice: Subject to any disclaimer, the term of this patent is extended or adjusted under 35 U.S.C. 154(b) by 853 days.

(21) Appl. No.: 15/735,036

(22) PCT Filed: Jun. 10, 2016

(86) PCT No.: PCT/US2016/036893
§ 371 (c)(1),
(2) Date: Dec. 8, 2017

(87) PCT Pub. No.: WO2016/201227
PCT Pub. Date: Dec. 15, 2016

(65) Prior Publication Data
US 2020/0030322 A1 Jan. 30, 2020

Related U.S. Application Data

(60) Provisional application No. 62/174,216, filed on Jun. 11, 2015.

(51) Int. Cl.
*A61K 31/496* (2006.01)
*A61P 7/06* (2006.01)

(52) U.S. Cl.
CPC .............. *A61K 31/496* (2013.01); *A61P 7/06* (2018.01)

(58) Field of Classification Search
None
See application file for complete search history.

(56) References Cited

U.S. PATENT DOCUMENTS

| | | | |
|---|---|---|---|
| 2,390,529 A | 12/1945 | Friedheim |
| 3,046,122 A | 7/1962 | Süs |
| 3,097,210 A | 7/1963 | Bicking |
| 3,755,322 A | 8/1973 | Winter et al. |
| 3,867,383 A | 2/1975 | Winter |
| 3,998,828 A | 12/1976 | Wiedermann |
| 4,084,053 A | 4/1978 | Desai et al. |
| 4,235,871 A | 11/1980 | Papahadjopoulos et al. |
| 4,315,940 A | 2/1982 | Hitzel et al. |
| 4,474,599 A | 10/1984 | Rogers et al. |
| 4,501,728 A | 2/1985 | Geho et al. |
| 4,591,548 A | 5/1986 | Delprato |
| 4,593,102 A | 6/1986 | Shanklin, Jr. |
| 4,775,762 A | 10/1988 | Knox et al. |
| 4,837,028 A | 6/1989 | Allen |
| 4,849,424 A | 7/1989 | Ikeda et al. |
| 4,881,965 A | 11/1989 | Yamamoto et al. |
| 4,889,553 A | 12/1989 | Rowson et al. |
| 4,959,094 A | 9/1990 | Wegner et al. |
| 5,019,369 A | 5/1991 | Presant et al. |
| 5,021,421 A | 6/1991 | Hino et al. |
| 5,122,530 A | 6/1992 | Tomioka et al. |
| 5,180,732 A | 1/1993 | Tomioka et al. |
| 5,220,028 A | 6/1993 | Iwasawa et al. |
| 5,252,590 A | 10/1993 | Tomioka et al. |
| 5,489,591 A | 2/1996 | Kobayashi et al. |
| 5,556,866 A | 9/1996 | Aga et al. |
| 5,807,876 A | 9/1998 | Armistead et al. |
| 5,834,485 A | 11/1998 | Dyke et al. |
| 5,843,485 A | 12/1998 | Fernandez et al. |
| 5,962,490 A | 10/1999 | Chan et al. |
| 5,965,559 A | 10/1999 | Faull et al. |
| 5,965,569 A | 10/1999 | Camps Garcia et al. |
| 5,984,882 A | 11/1999 | Rosenschein et al. |
| 6,020,357 A | 2/2000 | Pinto et al. |
| 6,106,849 A | 8/2000 | Malkan et al. |
| 6,150,356 A | 11/2000 | Lloyd et al. |
| 6,172,005 B1 | 1/2001 | Selby |
| 6,262,113 B1 | 7/2001 | Widdowson et al. |
| 6,265,588 B1 | 7/2001 | Mullner et al. |
| 6,274,620 B1 | 8/2001 | Labrecque et al. |
| 6,313,127 B1 | 11/2001 | Waterson et al. |
| 6,399,358 B1 | 6/2002 | Williams et al. |
| 6,492,368 B1 | 12/2002 | Dorsch et al. |
| 6,511,977 B1 | 1/2003 | Lloyd et al. |
| 6,723,730 B2 | 4/2004 | Bakthavatchalam et al. |

(Continued)

FOREIGN PATENT DOCUMENTS

| | | | |
|---|---|---|---|
| CA | 2235621 A1 | 5/1997 |
| CN | 101296909 A | 10/2008 |

(Continued)

OTHER PUBLICATIONS

Zacks Equity Research Jun. 10, 2014 (Year: 2014).*

(Continued)

*Primary Examiner* — Jeffrey S Lundgren
*Assistant Examiner* — Michael J Schmitt
(74) *Attorney, Agent, or Firm* — Goodwin Procter LLP

(57) ABSTRACT

Described herein are methods for using compounds that activate pyruvate kinase.

16 Claims, 16 Drawing Sheets

(56) References Cited

U.S. PATENT DOCUMENTS

| | | | |
|---|---|---|---|
| 6,818,631 B1 | 11/2004 | Nakagawa et al. |
| 6,979,675 B2 | 12/2005 | Tidmarsh |
| 7,173,025 B1 | 2/2007 | Stocker et al. |
| 7,288,554 B2 | 10/2007 | Finkelstein et al. |
| 7,524,848 B2 | 4/2009 | Powers et al. |
| 7,572,913 B2 | 8/2009 | McKerracher et al. |
| 7,615,553 B2 | 11/2009 | Van Emelen et al. |
| 7,858,782 B2 | 12/2010 | Tao et al. |
| 7,863,444 B2 | 1/2011 | Calderwood et al. |
| 8,058,313 B2 | 11/2011 | Reddy et al. |
| 8,133,900 B2 | 3/2012 | Hood et al. |
| 8,465,673 B2 | 6/2013 | Yasuda et al. |
| 8,642,660 B2 | 2/2014 | Goldfarb |
| 8,742,119 B2 | 6/2014 | Salituro et al. |
| 8,785,450 B2 | 7/2014 | Salituro et al. |
| 8,889,667 B2 | 11/2014 | Salituro et al. |
| 9,193,701 B2 | 11/2015 | Su |
| 9,199,968 B2 | 12/2015 | Salituro et al. |
| 9,404,081 B2 | 8/2016 | Su |
| 9,682,080 B2 | 6/2017 | Su |
| 9,980,961 B2 | 5/2018 | Su et al. |
| 10,029,987 B2 | 7/2018 | Salituro et al. |
| 10,632,114 B2 | 4/2020 | Su et al. |
| 2002/0188027 A1 | 12/2002 | Robinson et al. |
| 2003/0082877 A1 | 5/2003 | Ootsuka et al. |
| 2003/0095958 A1 | 5/2003 | Bhisetti et al. |
| 2003/0106381 A1 | 6/2003 | Krouth et al. |
| 2003/0109527 A1 | 6/2003 | Jin et al. |
| 2003/0158232 A1 | 8/2003 | Cheng et al. |
| 2003/0187001 A1 | 10/2003 | Calderwood et al. |
| 2003/0207882 A1 | 11/2003 | Stocker et al. |
| 2003/0213405 A1 | 11/2003 | Harada et al. |
| 2004/0048283 A1 | 3/2004 | Pau et al. |
| 2004/0067234 A1 | 4/2004 | Einat et al. |
| 2004/0152648 A1 | 8/2004 | Ullrich et al. |
| 2004/0198979 A1 | 10/2004 | Dhanak et al. |
| 2004/0235755 A1 | 11/2004 | Eigenbrodt et al. |
| 2004/0248221 A1 | 12/2004 | Stockwell |
| 2005/0176675 A1 | 8/2005 | Gorny |
| 2006/0084645 A1 | 4/2006 | Pal et al. |
| 2006/0281122 A1 | 12/2006 | Bryant et al. |
| 2007/0032418 A1 | 2/2007 | Shapiro et al. |
| 2007/0127505 A1 | 6/2007 | Laurila et al. |
| 2007/0244088 A1 | 10/2007 | Brickmann et al. |
| 2007/0280918 A1 | 12/2007 | Schwartz et al. |
| 2008/0004269 A1 | 1/2008 | Xu et al. |
| 2008/0021116 A1 | 1/2008 | Ullrich et al. |
| 2008/0044833 A1 | 2/2008 | Connors |
| 2008/0051414 A1 | 2/2008 | Hurley et al. |
| 2008/0214495 A1 | 9/2008 | Alstermark et al. |
| 2008/0300208 A1 | 12/2008 | Einat et al. |
| 2009/0048227 A1 | 2/2009 | Chakravarty et al. |
| 2009/0054453 A1 | 2/2009 | Alcaraz et al. |
| 2009/0093526 A1 | 4/2009 | Miller et al. |
| 2009/0163508 A1 | 6/2009 | Kori et al. |
| 2009/0163545 A1 | 6/2009 | Goldfarb |
| 2009/0247499 A1 | 10/2009 | Fletcher et al. |
| 2009/0270454 A1 | 10/2009 | Weingarten et al. |
| 2010/0105657 A1 | 4/2010 | Nordvall et al. |
| 2010/0129350 A1 | 5/2010 | Zacharie et al. |
| 2010/0144722 A1 | 6/2010 | Alexander et al. |
| 2010/0179150 A1 | 7/2010 | Basarab et al. |
| 2010/0273808 A1 | 10/2010 | Armitage et al. |
| 2010/0331307 A1* | 12/2010 | Salituro ............... C07D 271/12 |
| | | | 514/210.21 |
| 2011/0046083 A1 | 2/2011 | Cantley et al. |
| 2011/0073007 A1 | 3/2011 | Yasuda et al. |
| 2011/0086088 A1 | 4/2011 | Berry |
| 2011/0224252 A1 | 9/2011 | Dumeunier et al. |
| 2011/0288065 A1 | 11/2011 | Fujihara et al. |
| 2011/0312931 A1 | 12/2011 | Cioffi et al. |
| 2012/0121515 A1 | 5/2012 | Dang et al. |
| 2012/0122885 A1 | 5/2012 | Salituro et al. |
| 2012/0129865 A1 | 5/2012 | Wang et al. |
| 2012/0164143 A1 | 6/2012 | Teeling et al. |
| 2012/0172349 A1 | 7/2012 | Salituro et al. |
| 2012/0202818 A1 | 8/2012 | Tao et al. |
| 2012/0238576 A1 | 9/2012 | Tao et al. |
| 2012/0277233 A1 | 11/2012 | Tao et al. |
| 2013/0035329 A1 | 2/2013 | Saunders et al. |
| 2013/0109643 A1 | 5/2013 | Riggins et al. |
| 2013/0183281 A1 | 7/2013 | Su et al. |
| 2013/0184222 A1 | 7/2013 | Popovici-Muller et al. |
| 2013/0190249 A1 | 7/2013 | Lemieux et al. |
| 2013/0190287 A1 | 7/2013 | Cianchetta et al. |
| 2014/0155408 A1 | 6/2014 | Su |
| 2014/0187435 A1 | 7/2014 | Dang et al. |
| 2014/0194402 A1 | 7/2014 | Su |
| 2014/0249150 A1 | 9/2014 | Kung |
| 2014/0323467 A1 | 10/2014 | Salituro et al. |
| 2014/0323729 A1 | 10/2014 | Salituro et al. |
| 2015/0018328 A1 | 1/2015 | Konteatis et al. |
| 2015/0031627 A1 | 1/2015 | Lemieux et al. |
| 2015/0044716 A1 | 2/2015 | Balss et al. |
| 2015/0183760 A1 | 7/2015 | Salituro et al. |
| 2016/0106742 A1 | 4/2016 | Su |
| 2017/0166541 A1 | 6/2017 | Saunders et al. |
| 2017/0183311 A1 | 6/2017 | Salituro et al. |
| 2017/0290825 A1 | 10/2017 | Su |
| 2019/0345109 A1 | 11/2019 | Salituro et al. |

FOREIGN PATENT DOCUMENTS

| | | |
|---|---|---|
| CN | 101575408 A | 11/2009 |
| CN | 102659765 A | 9/2012 |
| CN | 103097340 A | 5/2013 |
| DE | 3314663 A1 | 10/1983 |
| DE | 3512630 A1 | 10/1986 |
| DE | 3813886 A1 | 11/1989 |
| DE | 19841985 A1 | 3/2000 |
| EP | 0022958 A1 | 1/1981 |
| EP | 0189069 A2 | 7/1986 |
| EP | 0246749 A2 | 11/1987 |
| EP | 0384228 A1 | 8/1990 |
| EP | 0385237 A2 | 9/1990 |
| EP | 0628551 A1 | 12/1994 |
| EP | 0945446 A1 | 9/1999 |
| EP | 1586558 A2 | 10/2005 |
| FR | 2735127 A1 | 12/1996 |
| GB | 1274436 A | 5/1972 |
| IT | 1176770 B | 8/1987 |
| JP | S61129129 A | 6/1986 |
| JP | H04099768 A | 3/1992 |
| JP | H06-025177 A | 2/1994 |
| JP | H07165708 A | 6/1995 |
| JP | H9291034 A | 11/1997 |
| JP | H11158073 A | 6/1999 |
| JP | 2002193710 A | 7/2002 |
| JP | 2004107220 A | 4/2004 |
| JP | 2007238458 A | 9/2007 |
| JP | 2008514590 A | 5/2008 |
| JP | 2009237115 A | 10/2009 |
| JP | 2010079130 A | 4/2010 |
| JP | 2010181540 A | 8/2010 |
| JP | 4753336 B2 | 8/2011 |
| JP | 2014509458 A | 4/2014 |
| JP | 2014509459 A | 4/2014 |
| WO | 8501289 A1 | 3/1985 |
| WO | 1992011761 A1 | 7/1992 |
| WO | 9313072 A1 | 7/1993 |
| WO | 1996030343 A1 | 10/1996 |
| WO | 9728128 A1 | 8/1997 |
| WO | 9728129 A1 | 8/1997 |
| WO | 9728141 A1 | 8/1997 |
| WO | 1997044322 A1 | 11/1997 |
| WO | 9803350 A1 | 1/1998 |
| WO | 199916751 A1 | 4/1999 |
| WO | 9932463 A1 | 7/1999 |
| WO | 1999048490 A1 | 9/1999 |
| WO | 990062506 A1 | 12/1999 |
| WO | 00/17202 A1 | 3/2000 |
| WO | 0053596 A2 | 9/2000 |
| WO | 0107440 A1 | 2/2001 |
| WO | 2001016097 A1 | 3/2001 |

(56) References Cited

FOREIGN PATENT DOCUMENTS

| | | |
|---|---|---|
| WO | 2001019788 A2 | 3/2001 |
| WO | 2001019798 A2 | 3/2001 |
| WO | 2001064642 A2 | 9/2001 |
| WO | 2001064643 A2 | 9/2001 |
| WO | 2002072077 A2 | 9/2002 |
| WO | 02095063 A1 | 11/2002 |
| WO | 2002100822 A1 | 12/2002 |
| WO | 2002102313 A2 | 12/2002 |
| WO | 030016289 A1 | 2/2003 |
| WO | 0322277 A1 | 3/2003 |
| WO | 03037252 A2 | 5/2003 |
| WO | 03062235 A1 | 7/2003 |
| WO | 03076422 A1 | 9/2003 |
| WO | 2003073999 A2 | 9/2003 |
| WO | 2003093297 A2 | 11/2003 |
| WO | 2004004730 A2 | 1/2004 |
| WO | 2004009562 A1 | 1/2004 |
| WO | 2004014851 A2 | 2/2004 |
| WO | 2004037251 A1 | 5/2004 |
| WO | 2004046120 A2 | 6/2004 |
| WO | 2004050033 A2 | 6/2004 |
| WO | 2004073619 A2 | 9/2004 |
| WO | 2004074438 A2 | 9/2004 |
| WO | 2004089470 A2 | 10/2004 |
| WO | 2004110375 A2 | 12/2004 |
| WO | 2005035507 A2 | 4/2005 |
| WO | 2005060956 A1 | 7/2005 |
| WO | 2005065691 A1 | 7/2005 |
| WO | 2005072642 A1 | 8/2005 |
| WO | 2005117591 A2 | 12/2005 |
| WO | 2005120474 A2 | 12/2005 |
| WO | 2006004195 A1 | 1/2006 |
| WO | 2006016062 A1 | 2/2006 |
| WO | 2006033628 A1 | 3/2006 |
| WO | 2006034341 A2 | 3/2006 |
| WO | 2006038594 A1 | 4/2006 |
| WO | 2006043950 A1 | 4/2006 |
| WO | 2006/052190 A1 | 5/2006 |
| WO | 2006063294 A2 | 6/2006 |
| WO | 2006070198 A1 | 7/2006 |
| WO | 2006077821 A1 | 7/2006 |
| WO | 2006079791 A1 | 8/2006 |
| WO | 2006117762 A2 | 11/2006 |
| WO | 2006122546 A1 | 11/2006 |
| WO | 2007003934 A2 | 1/2007 |
| WO | 2007023186 A1 | 3/2007 |
| WO | 2007117465 A2 | 10/2007 |
| WO | 2007127505 A2 | 11/2007 |
| WO | 2008019139 A2 | 2/2008 |
| WO | 2008024284 A2 | 2/2008 |
| WO | 2008026658 A1 | 3/2008 |
| WO | 2008047198 A1 | 4/2008 |
| WO | 2008050168 A1 | 5/2008 |
| WO | 2008052190 A2 | 5/2008 |
| WO | 2008070661 A1 | 6/2008 |
| WO | 2008073670 A2 | 6/2008 |
| WO | 2008076883 A2 | 6/2008 |
| WO | 2008131547 A1 | 11/2008 |
| WO | 2008154026 A1 | 12/2008 |
| WO | 2009012430 A1 | 1/2009 |
| WO | 2009013126 A1 | 1/2009 |
| WO | 2009016410 A2 | 2/2009 |
| WO | 2009025781 A1 | 2/2009 |
| WO | 2009053102 A1 | 4/2009 |
| WO | 2009086303 A2 | 7/2009 |
| WO | 2009/126863 A2 | 10/2009 |
| WO | 2009118567 A2 | 10/2009 |
| WO | 2009150248 A1 | 12/2009 |
| WO | 2010007756 A1 | 1/2010 |
| WO | 2010023445 A1 | 3/2010 |
| WO | 2010028099 A1 | 3/2010 |
| WO | 2010042867 A2 | 4/2010 |
| WO | 2010105243 A1 | 9/2010 |
| WO | 2010118063 A2 | 10/2010 |
| WO | 2010129596 A1 | 11/2010 |
| WO | 2010130638 A1 | 11/2010 |
| WO | 2010144338 A1 | 12/2010 |
| WO | 2010144404 A1 | 12/2010 |
| WO | 2011002816 A1 | 1/2011 |
| WO | 2011002817 A1 | 1/2011 |
| WO | 2011032169 A2 | 3/2011 |
| WO | 2011047432 A1 | 4/2011 |
| WO | 2011050210 A1 | 4/2011 |
| WO | 2011072174 A1 | 6/2011 |
| WO | 2011109441 A1 | 9/2011 |
| WO | 2011137089 A1 | 11/2011 |
| WO | 2012009678 A1 | 1/2012 |
| WO | 2012069503 A1 | 5/2012 |
| WO | 2012074999 A1 | 6/2012 |
| WO | 2012092442 A1 | 7/2012 |
| WO | 2012151451 A1 | 11/2012 |
| WO | 2012151452 A1 | 11/2012 |
| WO | 2012160034 A1 | 11/2012 |
| WO | WO-2012151451 A1 * | 11/2012 ........... A61K 31/535 |
| WO | 2012171506 A1 | 12/2012 |
| WO | 2013102431 A1 | 7/2013 |
| WO | 2013107291 A1 | 7/2013 |
| WO | 2013107405 A1 | 7/2013 |
| WO | 2013133367 A1 | 9/2013 |
| WO | 2014015422 A1 | 1/2014 |

OTHER PUBLICATIONS

Tuntland et al. "Implementation of pharmacokinetic and pharmacodynamics strategies in early research phases of drug discovery and developmental Novartis Institute of Biomedical Research," Frontiers in Pharmacology Jul. 28, 2014, p. 1-16 (Year: 2014).*

FDA Guidance, "Exposure-Response Relationships—Study Design, Data Analysis, and Regulatory Applications," Apr. 2003. (Year: 2003).*

STN File CA, Registry No. 338397-92-5, entered STN on May 25, 2001, Chemical Abstracts Index Name "1H-Pyrrole-2-sulfonamide, 1-[3-chloro-5-(trifluoromethyl)-2-pyridinyl]-N,N-dimethyrl" Available though Key Organics (under the BIONET brand) Feb. 1993.

STN File CA, Registry No. 338397-95-8, entered STN on May 25, 2001, Chemical Abstracts Index Name "1H-Pyrrole-2-sulfonamide, N-[(4-chlorophenyl)-1-[3-chloro-5-(trifluoromethyl)-2-pyridinyl]" Available though Key Organics (under the BIONET brand) Feb. 1993.

STN File CA, Registry No. 338397-96-9, entered STN on May 25, 2001, Chemical Abstracts Index Name "1H-Pyrrole-2-sulfonic acid, 1-[3-chloro-5-(trifluoromethyl)-2-pyridinyl]-4-chlorophenyl ester" Available though Key Organics (under the BIONET brand) Feb. 1993.

STN File CA, Registry No. 338406-58-9, entered STN on May 25, 2001, Chemical Abstracts Index Name "1H-Pyrrole-2-sulfonamide, 1-[3-chloro-5-(trifluoromethyl)-2-pyridinyl]-N-[2-(trifluoromethyl)phenyl]" Available though Key Organics (under the BIONET brand) Mar. 1993.

STN File CA, Registry No. 338406-64-7, entered STN on May 25, 2001, Chemical Abstracts Index Name "1H-Pyrrole-2-sulfonamide, 1-[3-chloro-5-(trifluoromethyl)-2-pyridinyl]-N-(3-pyridinylmethyl)" Available though Key Organics (under the BIONET brand) Mar. 1993.

STN File CA, Registry No. 338406-72-7, entered STN on May 25, 2001, Chemical Abstracts Index Name "1H-Pyrrole-2-sulfonamide, N-[(4-chlorophenyl)methyl]-1-[3-chloro-5-(trifluoromethyl)-2-pyridinyl]" Available though Key Organics (under the BIONET brand) Mar. 1993.

STN File CA, Registry No. 338407-11-7, entered STN on May 25, 2001, Chemical Abstracts Index Name "1H=Pyrrole-2-sulfonamide, 1-[3-chloro-5-(trifluoromethyl)-2-pyridinyl]-N-[3-chloro-4-[[5-(trifluoromethyl)-2-pyridinyl]oxy]phenyl]" Available though Key Organics (under the BIONET brand) Mar. 1993.

STN File CA, Registry No. 338407-13-9, entered STN on May 25, 2001, Chemical Abstracts Index Name "Benzoic acid, 3-[[[1-[3-chloro-5-(trifluoromethyl)-2-pyridinyl]-1H-pyrrol-2-yl]sulfonyl]amino]" Available though Key Organics (under the BIONET brand) Mar. 1993.

(56) References Cited

OTHER PUBLICATIONS

STN File CA, Registry No. 380466-24-0 entered STN on Jan. 4, 2002, Chemical Abstracts Index Name "Benzenesulfonamide, N-methyl-N-phenyl-3-[[4-(2-pyridinyl)-1-piperazinyl]carbonyl]".
STN file CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 736168-79-9 entered STN on Aug. 31, 2004, Chemical Abstracts Index Name "Benzenesulfonamide, 3,4-difluoro-N-[3-334-(phenylmethyl0-1-piperazinyl]carbonyl]phenyl".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
STN Registry, L23 Answer 2 of 3 (CAS No. 1032450-21-7), Database: ASINEX Ltd.,Entered STN: Jul. 3, 2008 (Jul. 3, 2008).
STN Registry. L23 Answer 1 of 3 (CAS No. 1038821-72-5),Database: ChemDB (University of California Irvine), Entered STN: Aug. 5, 2008 (Aug. 5, 2008).
STN Tokyo, Registry No. 1001833-18-6, Entered STN on Feb. 6, 2008, Chemical Abstracts Index Name "1,4-Benzodioxin-6-sulfonamide, 2,3-dihydro-N-[4- [(4-methyl-1-piperazinyl)carbonyl]phenyl]—".
STN Tokyo, Registry No. 1030142-35-8, Entered STN on Jun. 24, 2008, Chemical Abstracts Index Name "1,4-Benzodioxin-6-sulfonamide, 2,3-dihydro-N-[4- [[4-[(5-methyl-3-isoxazolyl)methyl]-1-piperazinyl]carbonyl]phenyl]-".
STN Tokyo, Registry No. 1031531-78-8, Entered STN on Jun. 29, 2008 Chemical Abstracts Index Name "1,4-Benzodioxin-6-sulfonamide, N-4[4-[(4-acetyl-1-piperazinyl)carbonyl]phenyl]-2,3-dihydro-".
STN Tokyo, Registry No. 1057928-35-4, Entered STN on Oct. 7, 2008, Chemical Abstracts Index Name "1,4-Benzodioxin-6-sulfonamide, 2,3-dihydro-N-[4- [[4-(2-pyridinyl)-1-piperazinyl]carbonyl]phenyl]-".
STN Tokyo, Registry No. 1240875-00-6, entered STN on Sep. 14, 2010, Chemical Abstracts Index Name "1,4-Benzodioxin-6-sulfonamide, 2,3-dihydro-N-[4-[[4-(2-thiazolyl)-1-piperazinyl]carbonyl]phenyl]-".
STN Tokyo, Registry No. 748791-86-8, Entered STN on Sep. 21, 2004, Chemical Abstracts Index Name "1,4-Benzodioxin-6-sulfonamide, N-[4- [[4-(2-furanylcarbonyl)-1-piperazinyl]carbonyl]phenyl]-2,3-dihydro-".
STN Tokyo, Registry No. 878469-24-0, Entered STN on Mar. 29, 2006, Chemical Abstracts Index Name "1,4-Benzodioxin-6-sulfonamide, 2,3-dihydro-N-[4-[[4-(2-pyrimidinyl)-1-piperazinyl]carbonyl]phenyl]-".
STN Tokyo, Registry No. 878474-39-6, Entered STN on Mar. 29, 2006, Chemical Abstracts Index Name "1,4-Benzodioxin-6-sulfonamide, 2,3-dihydro-N-[4[(4-phenyl-1-piperazinyl)carbonyl]phenyl]-".
STN Tokyo, Registry No. 878590-33-1, Entered STN on Mar. 30, 2006, Chemical Abstracts Index Name "1,4-Benzodioxin-6-sulfonamide, 2,3-dihydro-N-[4-[{4-(tetrahydro-2-furanyl)methyl]-1-piperazinyl]carbonyl]phenyl]-".
STN Tokyo, Registry No. 878943-66-9 Entered STN on Apr. 2, 2006, Chemical Abstracts Index Name "1,4-Benzodioxin-6-sulfonamide, 3,4-dihydro-N-[[4-(2-pyrimidinyl)-1-piperazinyl]carbonyl]phenyl]-".
STN Tokyo, Registry No. 878956-06-0, Entered STN on Apr. 2, 2006, Chemical Abstracts Index Name "1,4-Benzodioxin-6-sulfonamide, N-[4- [[4-(cyclopropylcarbonyl)-1-piperazinyl]carbonyl]phenyl]-2,3-dihydro-".
STN Tokyo, Registry No. 920679-46-5, Entered STN on Feb. 13, 2007, Chemical Abstracts Index Name "1,4-Benzodioxin-6-sulfonamide, 2,3-dihydro-N-[4- [[4-(4-pyridinyl)-1-piperazinyl]carbonyl]phenyl]-".
STN Tokyo, Registry No. 920822-52-2, Entered STN on Feb. 14, 2007, Chemical Abstracts Index Name "1,4-Benzodioxin-6-sulfonamide, N-[4- [[4-(4-fluoropheyl)-1-piperazinyl]carbonyl]phenyl]-2,3dihydro-".
STN Tokyo, Registry No. 920824-56-2, Entered STN on Feb. 14, 2007, Chemical Abstracts Index Name "1,4-Benzodioxin-6-sulfonamide, 2,3-dihydro-N-[4- [[4-(3-thienylmethyl)-1-piperazinyl]carbonyl]phenyl]-".
STN Tokyo, Registry No. 920847-34-3, Entered STN on Feb. 14, 2007, Chemical Abstracts Index Name "1,4-Benzodioxin-6-sulfonamide, 2,3-dihydro-N-[4- [[4-(2-methylphenyl)-1-piperazinyl]carbonyl]phenyl]-".
STN Tokyo, Registry No. 920875-39-4, Entered STN on Feb. 14, 2007, Chemical Abstracts Index Name "1,4-Benzodioxin-6-sulfonamide, 2,3-dihydro-N-[4- [[4-(2-hydroxyphenyl)-1-piperazinyl]carbonyl]phenyl]-".
STN Tokyo, Registry No. 920902-88-1, Entered STN on Feb. 14, 2007, Chemical Abstracts Index Name "1,4-Benzodioxin-6-sulfonamide, 2,3-dihydro-N-[4- [[4-(2-thienylmethyl)-1-piperazinyl]carbonyl]phenyl]-".
STN Tokyo, Registry No. 920921-09-1 Entered STN on Feb. 14, 2007, Chemical Abstracts Index Name "2H-1, 5-Benzodioxepin-7-sulfonamide, 3,4-dihydro-N-[4-[[4-(2pyridinyl)-1-piperazinyl]carbonyl]phenyl]-".
STN Tokyo, Registry No. 920924-42-1, Entered STN on Feb. 14, 2007, Chemical Abstracts Index Name "1,4-Benzodioxin-6-sulfonamide, 2,3-dihydro-N-[4- [[4-(2-pyridinylmethyl)-1-piperazinyl]carbonyl]phenyl]-".
STN Tokyo, Registry No. 941220-77-5, Entered STN on Jul. 4, 2007, Chemical Abstracts Index Name "2H-1, 5-Benzodioxepin-7-sulfonamide, 3,4-dihydro-N-[4-[(4-methyl-1-piperazinyl)carbonyl]phenyl]-".
Struys et al, Investigations by mass isotopomer analysis of the formation of D-2-hydroxyglutarate by cultured lymphoblasts from two patients with D-2-hydroxyglutaric aciduria, FEBS letters 92004 vol. 557, pp. 115-120.
Struys et al. "Mutations in the D-2-hydroxyglutarate dehydrogenase gene cause D-2-hydroxyglutaric aciduria" American Journal of Human Genetics, 2005. 76:358-360.
Struys, Ea. et al. "Measurement of Urinary D- and L-2-Hydroxyglutarate Enantiomers by Stable-Isotope-Dilution LiquidChromatography-Tandem Mass Spectrometry after Derivatization with Diacetyi-L-Tartaric Anhydride." Clinical Chemistry (2004)501391-1395.
Surh, "Cancer Chemoprevention with Dietary Phytochemicals", Nature Reviews Cancer, Nature Publishing Group, vol. 3, p. 768-780, 2003.
Szoka et al., "Comparative properties and methods of preparation of lipid vesicles (liposomes )," Ann. Rev. Biophys. Bioeng., 9, 467-508 (1980).
Takagi et al. "Synthesis of poly(triazinylstyrene) containing nitrogen-bawed ligand and function as metal ion adsorbent and oxidation catalyst" Reactive & Functional Polymers (2006) vol. 31, pp. 1718-1724.
Takashi Yamaoka, Adenosine deaminase hyperkinasia, Nihon Rinsho (supplementary volume) series of Syndrome for each area 20 Blood Syndrome I, Aug. 12, 1998, p. 308-311.
Tawaka, et al., Caplus an 1998:794998.
The radiation fact sheet published by the National Cancer Institute, http://www.cancer.gov/about-cancer/treatment/types/radiation-therapy/radiation-fact-sheet, reviewed Jun. 30, 2010.
Thompson, "Metabolic Enzymes as Oncogenes or Tumor Suppressors." The New England 18-22 Journal of Medicine, Feb. 19, 2009, vol. 360, No. 8, pp. 813-815; p. 813, p. 815, col. 1; Fig 1.
Uozumi et al., "Catalytic asymmetric construction of morpholines and piperazines by palladium-catalyzed tandem allylic substitution reactions," J. Org. Chem., 58 (24),6826-6832 (1993).
Van Schaftingen et al. "L-2-Hydroglutaric aciduria, a disorder of metabolite repair" J Inherit. Metab. Dis. (2009) vol. 32, pp. 135-142.
Vander Heiden et al., "Growth Factors Can Influence Cell Growth and Survival Through Effects on Glucose Metabolism," Mol Cell Biol. 21: 5899-5912 (2001).

(56) References Cited

OTHER PUBLICATIONS

Vander Heiden et al., "Identification of Small Molecule Inhibitors of Pyruvate Kinase M2," Biochemical Pharmacology. 79(8): 1118-1124 (2010).
Villen et al., "Large-Scale Phosphorylation Analysis of Mouse Liver," Proc Nat! Acad Sci USA 104: 1488-1493 (2007).
Park, "Prevention of type 2 diabetes mellitus from the viewpoint of genetics." Diabetes Research and Clinical Practice 2004; 66S: S33-S35.
Paronikyan et al. "Synthesis and biological activity of 3-piperazinylpyrano [3,4-C] pyridines" Armyanskii Khimicheskii Zhurnal (1990) vol. 43, No. 8, pp. 518-523.
Parsons et al. "An Integrated Genomic Analysis of Human Glioblastoma Multiforme" Science vol. 321 (2008) pp. 1807-1812 and Supplemental Data.
Patel et al. "Synthesis of some new idolinone derivatives containing piperazine moiety" Bulgarian Chemical Communications, 2003 Bol 35 No. 4 pp. 242-244.
Paudler et al., "3,7-Disubstituted octahydro-1,5-diazocines. Their conversion into tetrahydro-1,5-diazocines and into ring-contracted products," J. Org. Chem., 32 (8), 2425-2430 (1967).
Petz et al. "Increased IgG Molecules Bound to the Surface of Red Blood Cells of Patients With Sickle Cell Anemia" Blood (1984) vol. 64, No. 1, pp. 301-304.
Pollard et al., "Some Amides of Piperazines," J. Am. Chem. Soc., 75 (2), 491 (1953).
Pollard et al., "Cancer. Puzzling patterns of predisposition." Science. Apr. 10, 2009, vol. 324, 1-5,15-16, 18-22,35-38 No. 5924, pp. 192-194.
Popovici-Muller, Janeta et al. Discovery of the First Potent Inhibitors of Mutant IDH1 That Lower Tumor2-HG in Vivo. ACS Medicinal Chemistry Letters. Sep. 17, 2012 (Sep. 17, 2012), vol. 3, No. 10, 850-855.
Proisy et al. "Rapid Synthesis of 3-Aminoisoquinoline-5-sulfonamides Using the Buchwald-Hartwig Reaction" Synthesis 2009, No. 4, pp. 0561-0566.
Pubchem CID 4078245 [online]; Sep. 13, 2005 [retrieved on Feb. 4, 2012]; retrieved from http://pubchem.ncbi.nim.nih.gov/; 2d-structure.
Pubchem CID 4854170 [online]; Sep. 17, 2005 [retrieved on Feb. 4, 2012]; retrieved from http://pubchem.ncbi.nim.nih.gov/; 2d-structure.
Pujol, et. al., "Is there a case for cisplatin in the treatment of smallcell lung cancer? A meta-analysis of randomized trials of a cisplatin-containing regimen versus a regimen without this alkylating agent" British Journal of Cancer, Cancer Research Campaign, vol. 83, issue 1, pp. 8-15, 2000.
Rao et al., "Polymorphism in Drugs and its Significance in Therapeutics". Journal of Scientific & Industrial Research vol. 46 Oct. 1987 pp. 450-455.
Raynaud et al. "Absence of R140Q Mutation of Isocitrate Dehydrogenase 2 in Gliomas and Breast Cancers" Oncology Letters (2010) vol. 1, No. 5, pp. 883-884.
Registry (STN) [online], Aug. 23, 2006 [Retrieved on Jan. 29, 2016] CAS Registration No. 903862-76-0.
Registry (STN) [online], Aug. 23, 2006 [Retrieved on Jan. 29, 2016] CAS Registration No. 903869-26-1.
Registry (STN) [online], Apr. 13, 2007 [Retrieved on Jan. 29, 2016] CAS Registration No. 929819-92-1.
Registry (STN) [online], Apr. 13, 2007 [Retrieved on Jan. 29, 2016] CAS Registration No. 929971-43-7.
Registry (STN) [online], Apr. 19, 2009 [Retrieved on Jan. 29, 2016] CAS Registration No. 1136498-70-8.
Registry (STN) [online], Aug. 27, 2009 [Retrieved on Jan. 29, 2016] CAS Registration No. 1176756-98-1.
Reitman et al. "Isocitrate Sehydrogenase 1 and 2 Mutations in Cancer: Alterations at a Crossroads of Cellular Metabolism" Journal of the National Cancer Institute, vol. 102, No. 13, pp. 932-941 (2010).
Remington's, "Structure Activity Relationship and Drug Design," Pharmaceutical Sciences, pp. 420-425p. 420-425, 1980.
Rich, et. al., "Development of novel targeted therapies in the treatment of malignant glioma" Nature Rev. Drug Disc., Nature Publishing Group, vol. 3, pp. 430-446, 2004.
Rohle et al. "An Inhibitor of Mutant IDH1 Delays Growth and Promotes Differentiation of Glioma Cells" Science, vol. 340, No. 6132 pp. 626-630 (2013).
Root et al., "Genome-Scale Loss-of-Function Screening with a Lentiviral RNAi Library," Nat Methods 3: 715-719 (2006).
Ruan et al., "HSP60, a protein downregulated by IGFBP7 in colorectal carcinoma." J Exp Clin Cancer Res.;29:41 (2010).
Sabatine et al., "Metabolomic Identification of Novel Biomarkers of Myocardial Ischemia," Circulation 112: 3868-3875 (2005).
Scharn et al. "Spatially Addressed Synthesis of Amino- and Amino-Oxy-Substituted 1,3,5-Triazine Arrays on Polymeric Membranes" Journal of Combinatorial Chemistry (2000) vol. 2, No. 4, pp. 361-369.
Schneider, et. al., "Tumor M2-pyruvate kinase in the follow-up of inoperable lung cancer patients: a pilot study." Cancer Letters, Elsevier, vol. 193, pp. 91-98, 2003.
Schroth et al., "RingschluBreaktion von Diacetylen mit Diaminen: Eine Ciniache von 2,3-Dihydro-1,4-diazepinen," Zeitschritt Fur Chemie., 6 (4), 143 (1969).
Seibel et al., "Synthesis and evaluation of B-lactams (piperazones) as elastase inhibitors," Bioorg. Med. Chern. Ltrs., 13 (3),387-389 (2003).
Shi, et al., "Silencing of pkm2 increases the efficacy of docetaxel in human lung cancer xenografts in mice." Cancer Science, vol. 101, # 6, 1447-1453, Jun. 2010.
Shih et al. "The Role of Mutations in Epigenetic Regulators in Myeloid Malignancies" Nature Reviews Cancer (2012) vol. 12, No. 9, pp. 599-612.
Sirkanyan, S.N. et al. Synthesis of new derivatives of piperazine-substituted pyrano[3,4-c]pyridines. Hayastani Kimiakan Handes 2009, vol. 62, No. 3-4 pp. 378-385. English Abstract Only.
Sonoda et al. "Analysis of IDH1 and IDH2 mutations in Japanese glioma patients" Cancer Science, vol. 100, No. 10, pp. 1996-1998.
Sosnovik et al. "Emerging concepts in molecular MRI." Curr. Op. Biotech., 2007, 18, 4-10.
Steiner et al. "Synthesis and Antihypertensive Activity of New 6-Heteroaryl-3-hydrazinopyridazine Derivatives" Journal of Medicinal Chemistry (1981) vol. 24, No. 1, pp. 59-63.
Stewart et al., "Piperazines. I. Derivatives of Piperazine-1-Carboxylic and-1,4-Dicarboxylic Acid,", J. Org. Chern., 18 (1), 1478-1483 (1953).
STN file CA, Registry No. 1023444-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylphenyl)-4-methyl-".
STN File CA, Registry No. 1090629-29-0, entered STN on Dec. 28, 2008, Chemical Abstracts Index Name "Benzenesulfonamide, 3-[[4-[(2,5-dimethoxyphenyl)methyl]-1-piperazinyl]carbonyl]-N-(4-methoxyphenyl)-4-methyl-".
STN File CA, Registry No. 134538-28-6, entered STN on Jun. 28, 1991, Chemical Abstracts Index Name "1H-Pyrano[3,4-c]pyridine-5-carbonitrile,3,4-dihydro-3,3-dimethyl-6-[4-(1-oxobutyl)-1-piperazinyl]-8-phenyl-", disclosed in Paronikyan et al. Armyanskii Khimicheskii Zhurnal, 1990, vol. 43, No. 8.
STN File CA, Registry No. 134538-29-7, entered STN on Jun. 28, 1991, Chemical Abstracts Index Name "1H-Pyrano[3,4-c]pyridine-5-carbonitrile,3,4-dihydro-3,3-dimethyl-6-[4-(2-methyl-1-oxopropyl)-1-piperazinyl]-8-phenyl-", disclosed in Paronikyan et al. Armyanskii Khimicheskii Zhurnal, 1990, vol. 43, No. 8.
STN File CA, Registry No. 134538-30-0, entered STN on Jun. 28, 1991, Chemical Abstracts Index Name "1H-Pyrano[3,4-c]pyridine-5-carbonitrile,6-(4-benzoyl-1-piperazinyl)-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 134538-31-1, entered STN on Jun. 28, 1991, Chemical Abstracts Index Name "1H-Pyrano[3,4-c]pyridine-5-carbonitrile,6-[4-(2-furanylcarbonyl)-1-piperazinyl]-3,4-dihydro-

(56) References Cited

OTHER PUBLICATIONS 3,3-dimethyl-8-phenyl-", disclosed in Paronikyan et al. Armyanskii Khimicheskii Zhurnal, 1990, vol. 43, No. 8.
STN File CA, Registry No. 321433-63-0, entered STN on Feb. 12, 2001, Chemical Abstracts Index Name "1H-Pyrrole-2-sulfonamide, 1-[3-chloro-5-(trifluoromethyl)-2-pyridinyl]-N-phenyl" Available though Key Organics (under the BIONET brand) Jan. 1994.
STN File CA, Registry No. 321433-64-1, entered STN on Feb. 12, 2001, Chemical Abstracts Index Name "1H-Pyrrole-2-sulfonamide, 1-[3-chloro-5-(trifluoromethyl)-2-pyridinyl]-N-(4-methphenyl)" Available though Key Organics (under the BIONET brand) Jan. 1994.
STN File CA, Registry No. 321433-65-2, entered STN on Feb. 12, 2001, Chemical Abstracts Index Name "1H-Pyrrole-2-sulfonamide, 1-[3-chloro-5-(trifluoromethyl)-2-pyridinyl]-N-(3,5-dimethylphenyl)" Available though Key Organics (under the BIONET brand) Jan. 1994.
STN File CA, Registry No. 321433-68-5, entered STN on Feb. 12, 2001, Chemical Abstracts Index Name "1H-Pyrrole-2-sulfonamide, 1-[3-chloro-5-(trifluoromethyl)-2-pyridinyl]-N-propyl" Available though Key Organics (under the BIONET brand) Jan. 1994.
STN File CA, Registry No. 321433-69-6, entered STN on Feb. 12, 2001, Chemical Abstracts Index Name "1H-Pyrrole-2-sulfonamide, 1-[3-chloro-5-(trifluoromethyl)-2-pyridinyl]-N-(2-methoxyethyl)" Available though Key Organics (under the BIONET brand) Jan. 1994.
Cohen-Solal et al. "A new sickle cell disease phenotype associating Hb S trait, severe pyruvate kinase deficiency (PK Conakry), and an a2 globin gene varient (Hb Conakry)," British Journal of Haematology, 1998, 103:950-956.
Dong et al. "PKM2 and cancer: The function of PKM2 beyond glycolosis (Review)," Oncology Letters, 2016, 11:1980-1986.
Aghili et al. "Hydroxyglutaric aciduria and malignant brain tumor: a case report and literature review", Journal of Neuroncology, 2008. 91:233-236.
Ansell et al. "The interactions of artificial coenzymes with alcohol dehydrogenase and other NAD(P)(H) dependent enzymes" Journal of Molecular Catalysis B: Enzymatic (1999) vol. 6, No. 1-2, pp. 111-123.
Avdeenko, et al., "Thiocyanation of N-arylsulfonyl-, N-aroyl-, and N-[(N-arylsulfonyl)benzimidoyl]-1,4-benzoquinone imines" Russian Journal of Organic Chemistry, vol. 45, No. 3 (2009), 408-416.
Balss, "Analysis of the IDH1 codon 132 mutation in brain tumors", Acata Neuropathol (2008) vol. 116, pp. 597-602.
Baxter I et al: "Preparation and some reactions of 6-arylsulphonimidobenzoxazol-2(3H)-one" Journal of the Chemical Society, Section C: Organic Chemistry, Chemical Society. Letchworth, GB LNKD-DOI:10.1039/J39700000850, Jan. 1, 1970 (Jan. 1, 1970), pp. 850-853.
Behun et al., "The Chemistry of Pyrazine and Its Derivatives. IV. The Alkylation and Arylation of Methylpyrazine," J Org. Chern., 26 (9),3379-3382 (1961).
Benesch et al., "The clinicopathological and prognostic relevance of pyruvate kinase M2 and pAkt expression in breast cancer." Anticancer Res.;30(5):1689-94 (2010).
Benner et al, "Evolution, language and analogy in functional genomics", Trends in Genetics (2001) vol. 17, pp. 414 418.
Berger, et. al., "Treatment of Pancreatic Cancer: Challenge of the Facts" World J. Surg., Societe Internationale de Chirurgie, vol. 27, pp. 1075-1083, 2003.
Beutler et al. "Elevated Pyruvate Kinase Activity in Patients with Hemolytic Anemia Due to Red Cell Pyruvate Kinase 'Deficiency'" The American Journal of Medicine (1987) vol. 83, pp. 899-904.
Bhushan et al. "Reversed-phase liquid chromatographic resolution of diastereomers of protein and non-protein amino acids prepared with newly synthesized chiral derivatizing reagents based on cyanuric chloride" Amino Acids (2011) vol. 40, pp. 403-409.
Bleeker et al., "IDH1 mutations at residue p. R132 (IDH1 (R132)) occur frequently in high-grade 18-22 gliomas but not in other solid tumors." Hum Muta1., Jan. 2009, vol. 30, No. 1, pp. 7-11.

Bonuccelli et al., "The reverse Warburg effect: Glycolysis inhibitors prevent the tumor promoting effects of caveolin-1 deficient cancer associated fibroblasts." Cell Cycle.;9(10) (2010).
Boxer, et al., "Evaluation of Substituted N,N?-Diarylsulfonamides as Activators of the Tumor Cell Specific M2 Isoform of Pyruvate Kinase", J Med Chem. Feb. 11, 2010; 53(3): 1048.
Boxer, et al., "Identification of activators for the M2 isoform of human pyruvate kinase Version 3", Sep. 2009, Probe Reports from the NIH Molecular Libraries Program [Internet]. Bethesda (MD): National Center for Biotechnology Information (US).
Braun et al. "Triazine-based polymers: 4. MALDI-MS of triazine-based polyamines" Polymer (1996) vol. 37, No. 5, pp. 777-783.
Budinger et al., "Cellular Energy Utilization and Supply During Hypoxia in Embryonic Cardiac Myocytes," Am J Physiol. 270: L44-53 (1996).
Buschow et al., "MHC class II-associated proteins in B-cell exosomes and potential functional implications for exosome biogenesis." Immunol Cell Biol. (2010).
Cairns et al. "Oncogenic Isocitrate Dehydrogenase Mutations: Mechanisms, Models, and Clinical Opportunities" Cancer Discovery (2013) vol. 3, Iss 7, pp. 730-741.
Cecil Textbook of Medicine, edited by Bennet, J.C., and Plum F., 20th edition, vol. 1, 1004-1010, 1996.
Chabner, et. al., "Chemotherapy and the war on cancer", Nature Rev. Cancer, Nature Publishing Group, vol. 5, pp. 65-72, 2005.
Chan et al., "Synthesis and characterization of poly(amide sulfonamide)s (PASAs)," J Polymer. Sci., 33 (15), 2525-2531 (1995).
Chan et al. "Multi-domain hydrogen-bond forming metal chelates: X-ray crystal structuresof dicyclopalladated 2,3-bis[6-(2-amino-4-phenylamino-1 ,3,5-triazinyl)]pyrazine(H2L) [Pd2Br2L] and 2,6-bis[6-(2-amino-4-phenylamino-1,3,5-triazinylium)] -pyridine dichloride" Chemical Communications (1996) No. 1, pp. 81-83.
Chapman et al. "Substituted aminopyrimidine protein kinase B (PknB) inhibitorsshow activity against *Mycobacterium tuberculosis*" Bioorganic Medicinal Chemistry Letters (2012) vol. 22, pp. 3349-3353.
Charache et al. "Effect of 2,3-Diphosphoglycerate on Oxygen Affinity of Blood in Sickle Cell Anemia" Journal of Clinical Investigation (1970) vol. 49, pp. 806-812.
Chen et al. " Cytotoxicity, Hemolysis, and Acute in Vivo Toxicity of Dendrimers Based on Melamine, Candidate Vehicles for Delivery" J. Am. Chem. Soc. (2004) vol. 126, No. 32, pp. 10044-10048.
Christofk et al., "Pyruvate Kinase M2 is a Phosphotyrosine-Binding Protein," Nature 452: 181-186 (2008).
Christofk et al. , "The M2 Splice Isoform of Pyruvate Kinase is Important for Cancer Metabolism and Tumour Growth," Nature 452: 230-233 (2008).
Clement, et. al., "Production of Intracellular Superoxide Mediates Dithiothreitol-Dependent Inhibition of Apoptotic Cell Death" Antioxidants and Redox Signaling, Mary Ann Liebert, vol. 7, issues 3-4, pp. 456-464, 2005.
Cocco et al. "Synthesis of Triflouromethylated Pyridinecarbonitriles" Journal of Heterocyclic Chemistry, 1995. vol. 32 pp. 543-545.
Cohen et al., "The development and therapeutic potential of protein kinase inhibitors", Current Opinion in Chemical Biology, 3,459-465, 1999.
Conti et al. "Su alcuni analoghi assigenati della benzo-tiazine 2-3-diidro-3-cheto-benzo-1-4-ossazine 6-sostitute" Bollettino Scientifico Della Facolta Di Chimica Industriale Di Bologna (1957) vol. XV, No. 2, pp. 33-36.
Crawford et al., Caplus an 2010:1218943.
Cuzick, et. al., "Overview of the main outcomes in breast-cancer prevention trials" The Lancet, The Lancet Publishing Group, vol. 361, pp. 296-300, 2003.
Dang et al., "Cancer-associated IDH1 mutations produce 2-hydroxyglutarate." Nature, 10 29-32 Dec. 2009, vol. 462, No. 7274, pp. 739-744.
Dang et al. "IDH Mutations in Glioma and Acute Myeloid Leukemia" Trends in Molecular Medicine (2010) vol. 16, No. 9, pp. 387-397.
Database Chemcats, Chemical Abstracts Service, Columbus, OH, US "Bionet Screening Compounds" Key Organics Ltd., Camelford, Cornwall (2001).

(56) References Cited

OTHER PUBLICATIONS

Davis et al. "Biochemical, Cellular, and Biophysical Characterization of a Potent Inhibitor of Mutant Isocitrate Dehydrogenase IDH1" The Journal of Biological Chemistry (2014) vol. 289, No. 20, pp. 13717-13725.
Denhem et al. "Blood diseases in the elderly," Moscow, Medicine, 1989, chapter 15.
Dermer et al., "Another Anniversary for the War on Cancer", Bio/Technology, 1994, 12:320.
Docoslis et al., "Characterization of the Distribution, Polymorphism, and Stability of Nimodipine in Its Solid Dispersions in Polyethylene Glycol by Micro-Raman Spectroscopy and Powder X-Ray Diffraction". The AAPS Journal 2007; 9 (3) Article 43, E361-E370.
Dohner et al. "Impact of Genetic Features on Treatment Decisions in AML" American Society of Hematology (2011) pp. 36-42.
Dombrauckas, et al., Structural Basis for Tumor Pyruvate Kinasa M2 Allosteric Regulation and Catalysis, Biochemistry, vol. 44, p. 9717-9429 (2005).
Dong et al. "PKM2 and cancer: The function of PKM2 beyond glycolisis," Oncology Letters, 2016, 11:1980-1986.
Duanmu et al. "Dendron-Functionalized Superparamagnetic Nanoparticles with Switchable Solubility in Organic and Aqueous Media: Matriced for Homogeneous Catalysis and Potential MRI Contrast Agents" Chem. Mater. (2006) vol. 18, No. 25, pp. 5973-5981.
Eigenbrodt et al., "Double Role for Pyruvate Kinase Type M2 in the Expansion of Phosphometabolite Pools Found in Tumor Cells," Crit Rev Oncog. 3: 91-115 (1992). (Abstract only).
Engelman et al., "Allelic Dilution Obscures Detection of a Biologically Significant Resistance Mutation in EGFR-Amplified Lung Cancer," J Clin Invest. 116: 2695-2706 (2006).
Eswaran et al., "Crystal Structures and Inhibitor Identification for PTPN5, PTPRR and PTPN7: A Family of Human MAPK-Specific Protein Tyrosine Phosphatases," Biochem J. 395: 483-491 (2006).
Fabbro et al. "Protein kinases as targets for anticancer agents: from inhibitors to useful drugs." Pharmacology & Therapeutics 93, 79-98, 2002.
Freshney et al.,Culture of Animal Cells, A Manual of Basic Technique, Alan R. Liss, Inc., 1983, New York, p. 4.
Anastasiou et al. "Pyruvate kinase M2 activators promote tetramer formation and suppress tumorigenesis," Nature Chemical Biology, 2012, 8(10):839-847.
Charles et al. "AG-348 activation of pyruvate in vivo enhances red cell glycolosis in mice," Database Biosis [Online], database accession No. PREV201500280942, vol. 124, No. 21, 56th Annual Meeting of the American Society of Hematology, San Francisco, CA, 2014.
Hua et al. "Phase I single (SAD) and multiple ascending dose (MAD) studies of the safety, tolerability, pharmacokinetics (PK) and pharmacodynamics (PD) of AG-348, a first-in-class allosteric activator of pyruvate kinase-R, in healthy subjects," Database Biosis [Online], database accession No. PREV201500280858, vol. 124, No. 21, 56TH Annual Meeting of the American Society-of-Hematology, San Francisco, CA, 2014.
Villoutreix et al., Caplus an 2010:20993.
Walsh et al. "2-oxo-N-aryl-1,2,3,4-tetrahydroquinoline-6-sulfonamides as activators of the tumor cell specific M2 isoform of pyruvate kinase" Bioorg Med Chem Lett. Nov. 1, 2011; 21(21): 6322-6327.
Wang et al "Facile Synthesis of 2,4-Dianiino-6-alkyi- or 6-Aryl-PyrimidineDerivatives" Journal of Heterocyclic Chemistry (2010) vol. 47 pp. 1056-1061.
Wang et al. "A novel ligand N,N?-di(2-pyridyl)-2,4-diamino-6-phenyl-1,3,5-triazine (dpdapt) and its complexes: [Cu(dpdapt)Cl2] and [Cu(dpdapt)(NO3)(H2O)] Â• NO3 Â• H2O" Polyhedron, 2006. vol. 25, Issue 1. pp. 195-202.
Ward, Patrick S, "The Common Feature of Leukemia-Associated IDH1 and IDH2 Mutations Is a Neomorphic Enzyme Activity Converting [alpha]-Ketoglutarate to 2-Hydroxyglutarate" Cancer cell, vol. 17,Nr:3,pp. 225-234, 2010.
Watanabe et al., "IDH1 Mutations Are Early Events in the Development of Astrocytomas and Oligodendrogliomas". American Journal of Pathology, Apr. 2009 (published online Feb. 26, 2009), vol. 174, No. 4, pp. 1149-1153; Abstract, p. 1150, col. 1.
Web posting, Pyruvate kinase M2 isozyme (PKM2), SciBX 5(42), Published online Oct. 25, 2012, Abstract only.
Wong et al. "PKM2, a Central Point of Regulation in Cancer Metabolism" International Journal of Cell Biology (2013) vol. 2013, pp. 1-11.
Written Opinion of International Search Authority for PCT/CN2013/000009 dated Apr. 18, 2013.
Yamada and Noguchi, "Nutrient and Hormonal Regulation of Pyruvate Kinase Gene Expression," Biochem J. 337:1-11 (1999).
Yan et al., "IDH1 and IDH2 Mutations in Gliomas." The New England Journal of Medicine, 19 Feb. 18-22, 2009, vol. 360, No. 8, pp. 765-773.
Yar et al., "An Annulation Reaction for the Synthesis of Morpholines, Thiomorpholines, and Piperazines from !3-Heteroatom Amino Compounds and Vinyl Sulfonium Salts," Angewandte Chemie., 47 (20),3784-3786 (2008).
Ye et al., Pyruvate kinase M2 promotes de novo serine synthesis to sustain mTORC1 activity and cell proliferation, PNAS 109(18), 2012, pp. 6904-6909.
Zhao et al: "Glioma-derived mutations in IDH1 dominantly inhibit IDH1 catalytic activity and induce HIF-1alpha", SCIENCE, vol. 324, No. 5924, Apr. 10, 2009 (Apr. 10, 2009), pp. 261-265.
Zheng et al. "Synthesis and antitumor evaluation of a novel series of triaminotriazine derivatives" Bioorganic & Medicinal Chemistry (2007) vol. 15, pp. 1815-1827.
Friedman et al., "Leptin and the regulation of body weight in mammals" Nature. vol. 395, 1996.
Furuya et al., Inactivation of the 3-phosphoglycerate dehydrogenase gene in mice: changes in gene expression and associated regulatory networks resulting from serine deficiency. Funct Integr Genomics (2008) 8:235-249.
Ge et al. "Anaplasma phagocytophilum inhibits human neutrophil apoptosis via upregulation of bfl-1, maintenance of mitochondrial membrane potential and prevention of caspase 3 activation." Cellular Microbiology, 2005, 7(1 ), 29-38.
Genetics Home Reference. "L2HGDH." accessed at <http://ghr.nlm.nih.gov/gene/L2HGDH> on Sep. 4, 2015.
Gewald et al. "Discovery of triazines as potent, selective and orally active PDE4 inhibitors" Bioorganic & medicinal Chemistry Letters (2013) vol. 23, pp. 4308-4314.
Golub et al., "Molecular Classification of Cancer: Class Discovery and Class Prediction by Gene Expression Monitoring", Science, 286, 531-537, 1999.
Gupta et al., "Dominant negative mutations affect oligomerisation of human pyruvate kinase M2 isozyme and promote cellular growth and polyploidy." J Biol Chem. (2010).
Hartmann et al. "Type and Frequency of IDH1 and IDH2 mutations are related to astrocytic and oligodendroglial differentiation and age: a study of 1010 diffuse gliomas" Acta Neuropathologica (2009) 118: 469-474.
Hitosugi, et al., "Tyrosine Phosphorylation Inhibits PKM2 to Promote the Warburg Effect and Tumor Growth" Sci. Signal., Nov. 17, 2009, vol. 2, Issue 97, p. ra73.
Holmes et al, 750 MHz 1H NMR spectroscopy characterisation of the complex metabolic pattern of urine from patients with inborn errors of metabolism: 2-hydroxyglutaric aciduria and maple syrup urine disease., Journal of Pharmaceutical and Biomedical Analysis (1997) vol. 15, pp. 1647-1659.
Hulleman, et al., "Pyruvate kinase M2 and prednisolone resistance in acute lymphoblastic leukemia." Haematologica. Sep. 2009; 94(9): 1322-1324.
Inglese et al., "Quantitative high-throughput screening: A titration-based approach that efficiently identifies biological activities in large chemical libraries," Proc. Natl. Acad. Sci., 103 (31), 11473-11478 (2006).

(56) References Cited

OTHER PUBLICATIONS

Irikura et al. "New s-Triazine Derivatives as Depressants for Reticuloendothelial Hyperfunction Induced by Bacterial Endotoxin" Journal of Medicinal Chemistry (2000) vol. 31, pp. 1081-1089.
Jennings et al, Expression and mutagenesis of mammalian cytosolic NADP+-specific isocitrate dehydrogenase, Biochemistry (1997)vol. 36, pp. 13743-13747.
Jiang et al., "Evaluation of thieno[3,2-b]pyrrole[3,2-d]pyridazinones as activators of the tumor cell specific M2 isoform of pyruvate kinase." Bioorg. Med. Chem. Lett., 20 (11), 3387-3393 (2010).
Joshi et al., "Age-related faecal calprotectin, lactoferrin and tumour M2-PK concentrations in healthy volunteers." Ann Clin Biochem.;47(Pt 3):259-63 (2010).
Jurica et al., "The Allosteric Regulation of Pyruvate Kinase by Fructose-1 ,6-Bisphosphate," Structure 6: 195-210 (1998).
Kaila et al. "A convenient one-pot synthesis of trisubstituted 1,3,5-triazines through intermediary amidinothioureas" Tetrahedron Letters (2010) vol. 51, pp. 1486-1489.
Kao et al., "A Small-Molecule Inhibitor of the Ribonucleolytic Activity of Human Angiogenin That Possesses Antitumor Activity," Proc. Nat!. Acad. Sci. USA, 99(15): 10066-10071 (2002).
Kelarev et al. "Synthesis and properties of sym-triazines. 10 Synthesis of 2,4-diamino-sym-triazines containing a sterically hindered phenol substituent" Chemistry of Heterocyclic Compounds (1992) vol. 28, No. 10, pp. 1189-1193.
Kharalkar et al., "Identification of Novel Allosteric Regulators of Human-Erythrocyte Pyruvate Kinase," Chem Biodivers. 4: 2603-2617 (2007).
Kim et al "Ser95, Asn97, and Thr78 are important for the catalytic function of porcine NADP-dependent isocitrate dehydrogenase" Protein Science (2005) 14: pp. 140-147.
Kim et al. "Identification and Functional Characterization of a Novel, Tissue-specific NAD1-dependent Isocitrate Dehydrogenase b Subunit Isoform" JBC. Dec. 24, 1999, vol. 274 No. 52 pp. 36866-36875.
Klapars et al., "A General and Efficient Copper Catalyst for the Amidation of Aryl Halides and the N-Arylation of Nitrogen Heterocycles," J. Am. Chem. Soc., 123 (31), 7727-7729 (2001).
Komoriya et al. "Design, synthesis, and biological activity of non-basic compounds as factor Xa inhibitors: SAR study of S1 and aryl binding sites" Bioorganic & Medicinal Chemistry 13 (2005) 3927-3954.
Koshelev et al. " Synthesis of 1-3,7 N-substituted 2,4-diamino-1,3,5-triazines containing pyridyl groups" Russian Journal of Organic Chemistry (1995) vol. 31, No. 2, pp. 260-263.
Kranendijk et al. "IDH2 Mutations in Patients with D-2-Hydroxyglutaric Aciduria" Science (2010) vol. 330, p. 336.
Krell et al., "IDH mutations in tumorigenesis and their potential role as novel therapeutic targets" Future Oncology (2013) vol. 9, Iss 12, pp. 1923-1935.
Kumar et al., "In vivo factors influencing tumour M2-pyruvate kinase level in human pancreatic cancer cell lines." Tumour Biol.;31(2):69-77 (2010).
Kumiko Tsujino et al., "CBA-Pk-1slc/Pk-1slcmutant mouse in Newborn period does not exhibit hemolytic anemia," Japanese Society of Animal Models for Human Diseases, 1998, vol. 14, p. 24.
Kung et al. "Small Molecule Activation of PKM2 in Cancer Cells Induces Serine Auxotrophy" Chemistry & Biology, 19, 1187-1198, Sep. 21, 2012.

Lee et al., "An Efficient Synthesis of 2,8-Diazabicyclo[4.3.0]-Nonane Derivatives Via Intramolecular Cyclization Reaction," Synth. Comm., 25 (23), 3741-3746 (1995).
Lee et al. "Combinatorial Solid-Phase Synthesis of 6-Aryl-1,3,4-triazines via Suzuki Coupling" Aust. J. Chem. (2011) vol. 64, pp. 540-544.
Lee, "Consolidation Effect of Phenylalanine-administration of Antitumor Activity of A 5 Fluorouracil," Med. J. Kagoshima Univ. 37(3-4): 285-308 (1985).
Lee, et al., "Pyruvate kinase isozyme type M2 (PKM2) interacts and cooperates with Oct-4 in regulating transcription" International J. Biochem. & Cell Biol., vol. 40, # 5,2008, 1043-1054.
Li et al., "Quantitative proteome analysis of multidrug resistance in human ovarian cancer cell line." J Cell Biochem.; 109(4):625-33 (2010).
Li et al., "Screening and identification of interactive proteins of SH2D4A." Yi Chuan.;32(7):712-8 (2010). (Abstract Only).
Liu et al. "Inhibition of Cancer-Associated Mutant Isocitrate Dehydrogenases: Synthesis, Structure-Activity Relationship, and Selective Antitumor Activity" Journal of Medicinal Chemistry (2014) vol. 57, pp. 8307-8318.
Lou. "IDH1: function follows form." SciBX, 2009, 1-2.
Luo et al. "Synthesis and Fungicidal Activity of N-Benzo[b][1,4]oxazin-6-yl-2,4-dimethylthiazole-5-carboxamides" Agrochemicals (2009) vol. 48, No. 1, pp. 19-22.
Lutker et al, "Crystal Polymorphism in a Carbamazepine Derivative: Oxcarbazepine". NIH Public Access. J Pharm Sci. Feb. 2010 ; 99(2): 794-803. doi: 10.1002/jps.21873.
Madsen-Duggan et al. "Lead optimization of 5.6-diarylpyridines as CB1 receptor inverse agonists" Bioorganic & Medicinal Chemistry Letters (2007) vol. 17, pp. 2031-2035.
Marry et al. "Human Biochemistry," Moscow, Mir, 1993, chapter 18.
Mass, R. D., "The HER receptor family: a rich target for therapeutic development", Int. J. Radiation Oncology Bio. Phys.vol. 58(3): 932-940, 2004.
May et al, How many species are there on earth, Science (1988) vol. 241, p. 1441.
Moreno et al. "Identification of diamine linkers with differing reactivity and their applicationin the synthesis of melamine dendrimers" Tetrahedron Letters (2008) vol. 49, pp. 1152-1154.
Moreno et al. "Molecular recognition in dendrimers based on melamine" Polymer Preprints (2005) vol. 46, No. 2, pp. 1127.
Morshed et al. "Computational approach to the identification of novel Aurora-A inhibitors" Bioorganic & Medicinal Chemistry (2011) vol. 19, No. 2, pp. 907-916.
Oeda, "On some 2,5-Dialikl-piperazines," Bull. Chem. Soc., 13, 465-470 (1938).
Pan et al. "Research Status of Pyruvate Deficiency" Chinese Journal of Hematology (1999) vol. 20, No. 4, pp. 223.
"Pyruvate Kinase Deficiency Natural History Study," ClinicalTrials. gov, 2014, 1-7.
Yang Hua et al. "Phase I Single (SAD) and Multiple Ascending Dose (MAD) Studies of the Safety, Tolerability, Pharmacokinetics (PK) and Pharmacodynamics (PD) of AG-348, a First-in-Class Allosteric Activator of Pyruvate Kinase-R, in Healthy Subjects," Blood, 2014, 124(21):1-3.
Yang Hua et al. "Phase I Single- and Multiple-Ascending-Dose Randomized Studies of the Safety, Pharmacokinetics, and Pharmacodynamics of AG-348, a First-in-Class Allosteric Activator of Pyruvate Kinase R, in Healthy Volunteers," Clinical Pharmacology in Drug Development, 2018, 00(0):1-14.

* cited by examiner

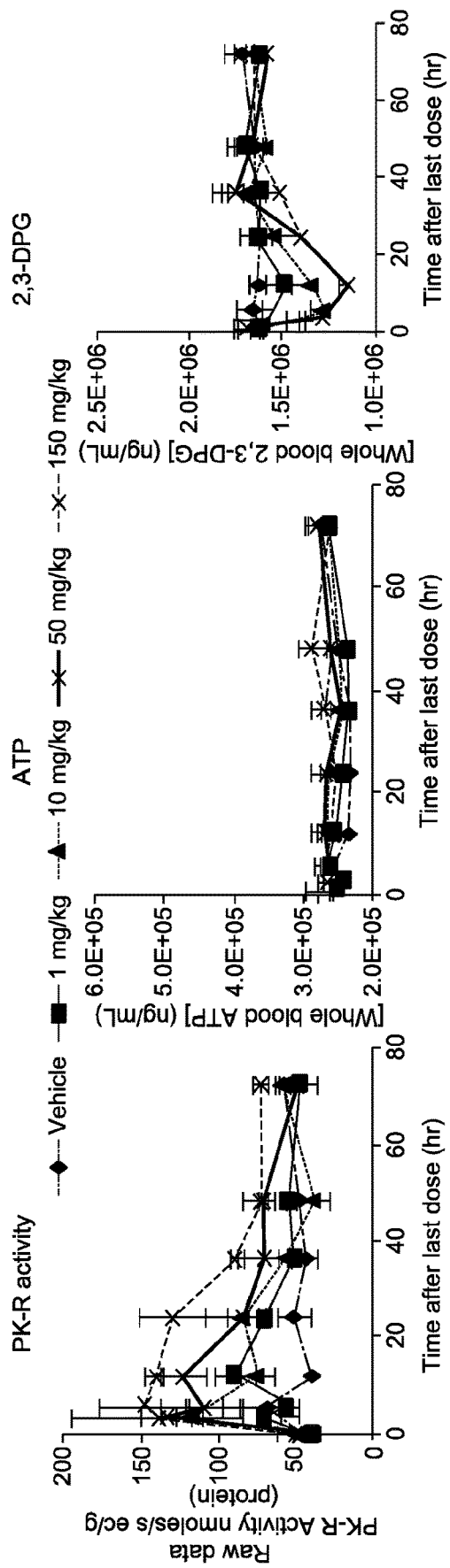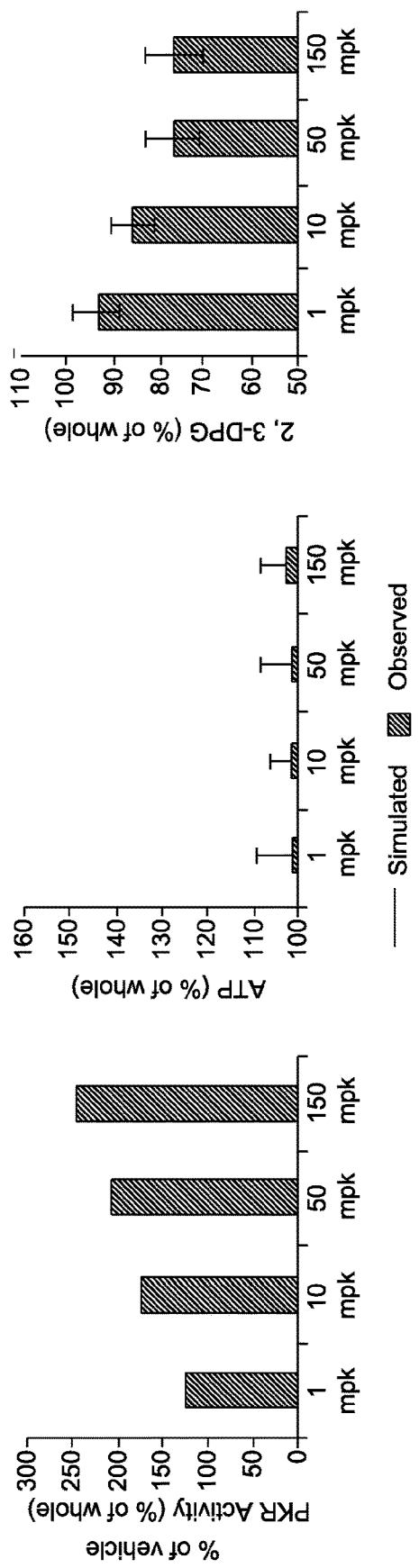
Figure 1

| Adverse event | Placebo (n=12) | Compound 1 (n=36) |
|---|---|---|
| Any AE, n (%) | 4 (33.3) | 16 (44.4) |
| Grade ≥ 3 | 0 | 0 |
| Any SAE, n (%) | 0 | 0 |
| AE leading to discontinuation, n (%) | 0 | 0 |
| Most common AEs (≥2 subjects in either group), n (%) | | |
| Headache | 3 (25.0) | 5 (13.9) |
| Nausea | 0 | 5 (13.9) |
| Vomiting | 0 | 2 (5.6) |
| Upper respiratory tract infection | 0 | 2 (5.6) |
| Treatment-related AE[a], n (%) | 2 (16.7) | 11 (30.6) |
| Most common treatment-related AEs [a] (≥2 subjects in either group), n (%) | | |
| Headache | 3 (25.0) | 4 (11.1) 1 at 30 mg, 2 at 1400 mg, 1 at 2500 mg |
| Nausea | 0 | 5 (13.9) 1 at 1400 mg, 4 at 2500 mg |
| Vomiting | 0 | 2 (5.6) 2 at 2500 mg |

[a] Judged possibly or probably related to treatment
AEs were graded usin National Cancer Institute Terminology Criteria for Adverse Events, Version 4.03

Figure 4

| Dose (mg) | $C_{max}$ (ng/mL) | $T_{max}$ (hr) | $AUC_{0-12}$ (hr·ng/mL) | $AUC_{0-\infty}$ (hr·ng/mL) | $t_{1/2}$ (hr) | Cl/F (L/hr) | Vz/F (L) |
|---|---|---|---|---|---|---|---|
| 30[a] | 461 (19.3) | 0.77 (0.48, 2.00) | 1679 (32.0) | 2079 (30.8) | 19.3 (18.9) | 14.4 (30.8) | 396 (30.1) |
| 120[a] | 2300 (43.9) | 1.01 (0.50, 3.00) | 8961 (32.0) | 11176 (32.9) | 17.8 (18.4) | 10.7 (32.9) | 271 (46.5) |
| 360[a] | 6637 (26.8) | 0.77 (0.50, 2.00) | 23501 (12.5) | 25944 (10.9) | 20.4 (17.6) | 13.9 (10.9) | 402 (23.8) |
| 700[a] | 12686 (17.7) | 1.49 (0.58, 3.03) | 61782 (25.9) | 68066 (27.9) | 79.3 (26.3) | 10.3 (27.9) | 1148 (29.4) |
| 1400[a] | 17688 (28.1) | 2.53 (1.72, 4.03) | 113348 (30.0) | 131493 (26.7) | 50.3 (29.5) | 10.6 (26.7) | 743 (36.3) |
| 2500[a] | 25477 (24.0) | 4.07 (0.48, 6.02) | 164122 (30.7) | 197795 (36.1) | 73.9 (68.5) | 12.6 (36.1) | 1163 (72.0) |

Geometric mean (geometric mean CV%). except $T_{max}$ which is median (minimum, maximum) and $t_{1/2}$ which is arithmetic mean (CV%)
N=6 for each dose level
[a]Samples collected through 72 hr
[b]Samples collected through 120 hr
$AUC_{0-12hr}$ = AUC from 0 to 12 hr; $AUC_{0-\infty}$ = AUC from 0 extrapolated to infinity; Cl/F = apparent clearance; $C_{max}$ = maximum concentration; $t_{1/2}$ = apparent terminal elimination half-life; $T_{max}$ = time of maximum observed concentration; Vz/F = apparent volume of distribution

Figure 6

METHODS OF USING PYRUVATE KINASE ACTIVATORS

CLAIM OF PRIORITY

This application is a national stage application under 35 U.S.C. 371 of International Application No. PCT/US2016/036893 filed Jun. 10, 2016, which claims priority from U.S. Ser. No. 62/174,216 filed Jun. 11, 2015. The entire contents of these applications are incorporated herein by reference in their entirety.

BACKGROUND

Pyruvate kinase deficiency (PKD) is one of the most common enzyme defects in erythrocytes in humans due to autosomal recessive mutations of the PKLR gene (Zanella, A., et al., *Br J Haematol* 2005, 130 (1), 11-25). It is also the most frequent enzyme mutation in the central glycolytic pathway and only second to glucose-6 phosphate dehydrogenase (G6PD) deficiency (Kedar, P., et al., *Clin Genet* 2009, 75 (2), 157-62) of the hexose monophosphate shunt.

Human erythrocytes are unique in that they anucleate when mature. Immature erythrocytes have nuclei but during early erythropoiesis prior to becoming circulating reticulocytes they extrude nuclei as well as other organelles such as mitochondria, endoplasmic reticulum, and Golgi apparatus, in order to make room for oxygen-carrying hemoglobin. As a result of lacking mitochondria, mature red blood cells do not utilize any of the oxygen they transport to economically synthesize adenosine triphosphate (ATP) as other normal differentiated cells do. Instead, red blood cells depend entirely on anaerobic glycolysis to cycle nicotinamide adenine dinucleotide ($NAD^+$) and to make ATP, an essential energy source largely used to drive ATPase-dependent $K^+/Na^+$ and $Ca^{2+}$ pumps, in order to maintain cell membrane integrity and pliability as they navigate through blood vessels. In PKD disorder, two major distinctive metabolic abnormalities are ATP depletion and concomitant increase of 2,3-diphosphoglycerate consistent with accumulation of upper glycolytic intermediates. Moreover, one of the consequences of decreased ATP and pyruvate levels is lowered lactate level leading to inability to regenerate $NAD^+$ through lactate dehydrogenase for further use in glycolysis. The lack of ATP disturbs the cation gradient across the red cell membrane, causing the loss of potassium and water, which causes cell dehydration, contraction, and crenation, and leads to premature destruction and diminished lifetime of the red blood cells (RBCs). Such defective RBCs are destroyed in the spleen, and excessive hemolysis rate in the spleen leads to the manifestation of hemolytic anemia. The exact mechanism by which PKD sequesters newly matured RBCs in the spleen to effectively shorten overall half-lives of circulating RBCs is not yet clear, but recent studies suggest that metabolic dysregulation affects not only cell survival but also the maturation process resulting in ineffective erythropoiesis (Aizawa, S. et al., *Exp Hematol* 2005, 33 (11), 1292-8).

Pyruvate kinase catalyzes the transfer of a phosphoryl group from phosphoenolpyruvate (PEP) to ADP, yielding one molecule of pyruvate and one molecule of ATP. The enzyme has an absolute requirement for $Mg^{2+}$ and $K^+$ cations to drive catalysis. PK functions as the last critical step in glycolysis because it is an essentially irreversible reaction under physiological conditions. In addition to its role of synthesizing one of the two ATP molecules from the metabolism of glucose to pyruvate, pyruvate kinase is also an important cellular metabolism regulator. It controls the carbon flux in lower-glycolysis to provide key metabolite intermediates to feed biosynthetic processes, such as pentose-phosphate pathway among others, in maintaining healthy cellular metabolism. Because of these critical functions, pyruvate kinase is tightly controlled at both gene expression and enzymatic allostere levels. In mammals, fully activated pyruvate kinase exists as a tetrameric enzyme. Four different isozymes (M1, M2, L and R) are expressed from two separate genes. Erythrocyte-specific isozyme PKR is expressed from the PKLR gene ("L gene") located on chromosome 1q21. This same gene also encodes the PKL isozyme, which is predominately expressed in the liver. PKLR consists of 12 exons with exon 1 is erythroid-specific whereas exon 2 is liver-specific. The two other mammalian isozymes PKM1 and PKM2 are produced from the PKM gene ("M gene") by alternative splicing events controlled by hnRNP proteins. The PKM2 isozyme is expressed in fetal tissues and in adult proliferating cells such as cancer cells. Both PKR and PKM2 are in fact expressed in proerythroblasts. However, upon erythroid differentiation and maturation, PKM2 gradually is decreased in expression and progressively replaced by PKR in mature erythrocytes.

Clinically, hereditary PKR deficiency disorder manifests as non-spherocytic hemolytic anemia. The clinical severity of this disorder ranges from no observable symptoms in fully-compensated hemolysis to potentially fatal severe anemia requiring chronic transfusions and/or splenectomy at early development or during physiological stress or serious infections. Most affected individuals, who are asymptomatic, paradoxically due to enhanced oxygen-transfer capacity, do not require any treatment. However, for some of the most severe cases, while extremely rare population-wise with estimated prevalence of 51 per million (Beutler, E. *Blood* 2000, 95 (11), 3585-8), there is no disease-modifying treatment available for these patients other than palliative care (Tavazzi, D. et al., *Pediatr Ann* 2008, 37 (5), 303-10). These hereditary non-spherocytic hemolytic anemia (HNSHA) patients present a clear unmet medical need.

Heterogenous genetic mutations in PKR lead to dysregulation of its catalytic activity. Since the initial cloning of PKR and report of a single point mutation $Thr^{384}$>Met associated with a HNSHA patient (Kanno, H. et al., *Proc Natl Acad Sci USA* 1991, 88 (18), 8218-21), there are now nearly 200 different reported mutations associated with this disease reported worldwide (Zanella, A. et al., *Br J Haematol* 2005, 130 (1), 11-25; Kedar, P., et al., *Clin Genet* 2009, 75 (2), 157-62; Fermo, E. et al., *Br J Haematol* 2005, 129 (6), 839-46; Pissard, S. et al., *Br J Haematol* 2006, 133 (6), 683-9). Although these mutations represent wide range genetic lesions that include deletional and transcriptional or translational abnormalities, by far the most common type is missense mutation in the coding region that one way or another affects conserved residues within domains that are structurally important for optimal catalytic function of PKR. The pattern of mutation prevalence seems to be unevenly distributed toward specific ethnic backgrounds. For instance, the most frequent codon substitutions reported for North American and European patients appear to be $Arg^{486}$>Trp and $Arg^{510}$>Gln, while mutations $Arg^{479}$>His, $Arg^{490}$>Trp and $Asp^{331}$>Gly were more frequently found in Asian patients (Kedar, P., et al., *Clin Genet* 2009, 75 (2), 157-62).

SUMMARY OF THE INVENTION

In one aspect, the present invention provides a method of evaluating a subject, the method comprising: administering to the subject N-(4-(4-(cyclopropylmethyl)piperazine-1-carbonyl)phenyl)quinoline-8-sulfonamide (Compound 1); and acquiring a value for the level of Compound 1, the level of 2,3-diphosphoglycerate (2,3-DPG), the level of adenosine triphosphate (ATP), or the activity of PKR in the subject, to thereby evaluate the subject.

In some embodiments, the value for the level of Compound 1 is acquired by analyzing the plasma concentration of Compound 1.

In some embodiments, the level of 2,3-DPG is acquired by analyzing the blood concentration of 2,3-DPG.

In some embodiments, the level of ATP is acquired by analyzing the blood concentration of ATP.

In some embodiments, the activity of PKR is acquired by analyzing the blood concentration of a $^{13}$C-label in the blood. For example, $^{13}$C-labeled glucose is administered to a subject, and incorporated into certain glycolytic intermediates in the blood.

In some embodiments, the analysis is performed by sample analysis of bodily fluid, such as blood, by e.g., mass spectroscopy, e.g. LC-MS.

In another aspect, the present invention provides a method of evaluating a subject, the method comprising acquiring, e.g., directly acquiring, the value for the level of a compound N-(4-(4-(cyclopropylmethyl)piperazine-1-carbonyl)phenyl) quinoline-8-sulfonamide (Compound 1), the level of 2,3-DPG, the level of ATP, or the activity of PKR in a subject that has been treated with Compound 1, to thereby evaluate the subject. In some embodiments, acquiring comprises receiving a sample from the subject. In some embodiments, acquiring comprises transmitting the value to another party, e.g., the party that administered Compound 1.

In some embodiments, the value for the level of Compound 1 is acquired by analyzing the plasma concentration of Compound 1.

In some embodiments, the level of 2,3-DPG is acquired by analyzing the blood concentration of 2,3-DPG.

In some embodiments, the level of ATP is acquired by analyzing the blood concentration of ATP.

In some embodiments, the activity of PKR is acquired by analyzing the blood concentration of $^{13}$C-label in the blood. For example, $^{13}$C-labeled glucose is administered to a subject, and incorporated into certain glycolytic intermediates in the blood.

In some embodiments, the analysis is performed by sample analysis of bodily fluid, such as blood, by e.g., mass spectroscopy, e.g. LC-MS.

In some embodiments, the subject has been administered Compound 1 within a preselected period of less than 7 days, less than 6 days, less than 5 days, less than 4 days, less than 3 days, or less than 72 hours prior to the evaluation, e.g., less than 48 hours, less than 24 hours, less than 12 hours, less than 10 hours, less than 8 hours, less than 6 hours, less than 4 hours, less than 3 hours, less than 2 hours, less than 1.5 hours, less than 1 hour, less than 45 minutes, less than 30 minutes, or less than 15 minutes.

In some embodiments, the subject has been administered Compound 1, e.g., orally, a dose of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg, of Compound 1.

In some embodiments, the subject has been administered Compound 1, e.g., orally, a dose of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In some embodiments, the subject has been administered, e.g., orally, Compound 1 once or twice daily.

In some embodiments, the subject has been administered Compound 1, e.g., orally, twice daily, e.g., about every 12 hours. In some embodiments, Compound 1 is administered to the subject at about 10 mg to about 1000 mg about every 12 hours, e.g., about 10 mg to about 60 mg about every 12 hours, about 60 mg to about 200 mg about every 12 hours, about 200 mg to about 500 mg about every 12 hours, about 500 mg to about 1000 mg about every 12 hours, e.g., about 15 mg about every 12 hours, about 60 mg about every 12 hours, about 120 mg about every 12 hours, about 360 mg about every 12 hours, about 700 mg about every 12 hours.

In some embodiments, the subject has been administered Compound 1, e.g., orally, once daily, e.g., about every 24 hours. In some embodiments, Compound 1 is administered, e.g., orally, to the subject at about 60 mg to about 200 mg about every 24 hours, e.g., about 90 mg about every 24 hours, about 120 mg about every 24 hours, about 150 mg about every 24 hours, about 180 mg about every 24 hours, or about 200 mg about every 24 hours.

In some embodiments, the method comprises comparing the level of Compound 1, the level of 2,3-DPG, or the level of ATP to a reference standard.

In some embodiments, the activity of PKR is acquired by analyzing the blood concentration of $^{13}$C-label in the blood. For example, $^{13}$C-labeled glucose is administered to a subject, and incorporated into certain glycolytic intermediates in the blood.

In some embodiments, the value for the level of Compound 1 is acquired by analyzing the plasma concentration of Compound 1.

In some embodiments, Compound 1 is present in a detectable amount in the subject at least 2 hours, at least 3 hours, at least 4 hours, at least 5 hours, at least 6 hours, at least 7 hours, at least 8 hours, at least 9 hours, or at least 10 hours after administration to the subject.

In some embodiments, the level of 2,3-DPG is acquired by analyzing the blood concentration of 2,3-DPG.

In some embodiments, the level of ATP is acquired by analyzing the blood concentration of ATP.

In some embodiments, the activity of PKR is acquired by analyzing the blood concentration of a $^{13}$C-label in the blood. For example, $^{13}$C-labeled glucose is administered to a subject, and incorporated into certain glycolytic intermediates in the blood.

In some embodiments, the analysis is performed by sample analysis of bodily fluid, such as blood, by e.g., mass spectroscopy, e.g. LC-MS.

In some embodiments, the reference standard for the level of Compound 1, the level of 2,3-DPG, the level of ATP, or the level of PRK activity is the level of Compound 1, the level of 2,3-DPG, the level of ATP, or the level of PRK activity prior to administration of Compound 1.

In some embodiments, the value for the level of Compound 1 is acquired by analyzing the plasma concentration of Compound 1.

In some embodiments, the level of 2,3-DPG is acquired by analyzing the blood concentration of 2,3-DPG.

In some embodiments, the level of ATP is acquired by analyzing the blood concentration of ATP.

In some embodiments, the activity of PKR is acquired by analyzing the blood concentration of a $^{13}$C-label in the blood. For example, $^{13}$C-labeled glucose is administered to a subject, and incorporated into certain glycolytic intermediates in the blood.

In some embodiments, the analysis is performed by sample analysis of bodily fluid, such as blood, by e.g., mass spectroscopy, e.g. LC-MS.

In some embodiments, the plasma concentration of Compound 1 is from about 10,000 ng/mL to about 1 ng/mL, e.g., about 1000 ng/mL to about 10 ng/mL.

In some embodiments, the blood concentration of 2,3-DPG is reduced by at least about 15% relative to the reference standard (e.g., from about 15% to about 60%). In some embodiments, the blood concentration of 2,3-DPG is reduced by at least about 15%, by at least about 20%, by at least about 25%, by at least about 30%, by at least about 35%, by at least about 40%, by at least about 45%, by at least about 50%, by at least about 55%, by at least about 60%.

In some embodiments, the blood concentration of 2,3-DPG is reduced for at least about 4 hours (e.g., at least about 8 hours, at least about 12 hours, at least about 16 hours, at least about 20 hours, at least about 24 hours, at least about 36 hours, at least about 48 hours, at least about 72 hours or longer).

In some embodiments, the blood concentration of 2,3-DPG is reduced by at least about 15% relative to the reference standard (e.g., from about 15% to about 60%). In some embodiments, the blood concentration of 2,3-DPG is reduced by at least about 15%, by at least about 20%, by at least about 25%, by at least about 30%, by at least about 35%, by at least about 40%, by at least about 45%, by at least about 50%, by at least about 55%, by at least about 60%, for at least about 4 hours (e.g., at least about 8 hours, at least about 12 hours, at least about 16 hours, at least about 20 hours, at least about 24 hours, at least about 36 hours, at least about 48 hours, at least about 72 hours or longer).

In some embodiments, the method comprises administering an amount of Compound 1 sufficient to provide a blood concentration of 2,3-DPG that is reduced by at least 15% relative to the reference standard (e.g., from about 15% to about 60%). In some embodiments, the blood concentration of 2,3-DPG is reduced by at least about 15%, by at least about 20%, by at least about 25%, by at least about 30%, by at least about 35%, by at least about 40%, by at least about 45%, by at least about 50%, by at least about 55%, by at least about 60%.

In some embodiments, a single administration of Compound 1 is sufficient to provide a blood concentration of 2,3-DPG reduced by at least 15% relative to the reference standard (e.g., from about 15% to about 60%). In some embodiments, the blood concentration of 2,3-DPG is reduced by at least about 15%, by at least about 20%, by at least about 25%, by at least about 30%, by at least about 35%, by at least about 40%, by at least about 45%, by at least about 50%, by at least about 55%, by at least about 60%.

In another aspect, the invention provides a method of treating a subject for a disorder, e.g., hereditary non-spherocytic hemolytic anemia; sickle cell anemia; thalassemia, e.g. beta-thalassemia; hereditary spherocytosis; hereditary elliptocytosis; sbetalipoproteinemia; Bassen-Kornzweig syndrome; or paroxysmal nocturnal hemoglobinuria, comprising administering to the subject an amount of Compound 1 sufficient to provide a blood concentration of 2,3-DPG reduced by at least 15% relative to the reference standard (e.g., from about 15% to about 60%). In some embodiments, the blood concentration of 2,3-DPG is reduced by at least about 15%, by at least about 20%, by at least about 25%, by at least about 30%, by at least about 35%, by at least about 40%, by at least about 45%, by at least about 50%, by at least about 55%, by at least about 60%.

In some embodiments, the reference standard is, e.g., the 2,3-DPG level or the blood ATP level, in a diseased human, e.g., a human having a metabolic disorder or a blood disorder, e.g., a human diagnosed with pyruvate kinase deficiency (PKD). In some embodiments, the reference standard is, e.g., a baseline level, e.g., the 2,3-DPG level or the blood ATP level, in the subject prior to administration with Compound 1.

In some embodiments, the blood concentration of 2,3-DPG is reduced for at least about 4 hours (e.g., at least about 8 hours, at least about 12 hours, at least about 16 hours, at least about 20 hours, at least about 24 hours, at least about 36 hours, at least about 48 hours, at least about 72 hours or longer).

In some embodiments, the subject has been administered Compound 1 within a preselected period of less than 7 days, less than 6 days, less than 5 days, less than 4 days, less than 3 days, or less than 72 hours prior to the evaluation, e.g., less than 48 hours, less than 24 hours, less than 12 hours, less than 10 hours, less than 8 hours, less than 6 hours, less than 4 hours, less than 3 hours, less than 2 hours, less than 1.5 hours, less than 1 hour, less than 45 minutes, less than 30 minutes, or less than 15 minutes.

In some embodiments, the subject is evaluated less than 72 hours, less than 48 hours, less than 24 hours, less than 12 hours, less than 10 hours, less than 8 hours, less than 6 hours, less than 4 hours, less than 3 hours, less than 2 hours, less than 1.5 hours, less than 1 hour, less than 45 minutes, less than 30 minutes, or less than 15 minutes, after administration of Compound 1.

In some embodiments, a single administration of Compound 1 is sufficient to provide a blood concentration of 2,3-DPG reduced by at least 15% relative to the reference standard (e.g., from about 15% to about 60%). In some embodiments, the blood concentration of 2,3-DPG is reduced by at least about 15%, by at least about 20%, by at least about 25%, by at least about 30%, by at least about 35%, by at least about 40%, by at least about 45%, by at least about 50%, by at least about 55%, by at least about 60%. In an embodiment, the blood concentration of 2,3-DPG is reduced for at least about 4 hours (e.g., at least about 8 hours, at least about 12 hours, at least about 16 hours, at least about 20 hours, at least about 24 hours, at least about 36 hours, at least about 48 hours, at least about 72 hours or longer).

In some embodiments, the subject has been administered Compound 1, e.g., orally, a dose of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg, of Compound 1.

In some embodiments, the subject has been administered Compound 1, e.g., orally, a dose of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In some embodiments, the subject has been administered, e.g., orally, Compound 1 once or twice daily.

In some embodiments, the subject has been administered Compound 1, e.g., orally, twice daily, e.g., about every 12 hours. In some embodiments, Compound 1 is administered to the subject at about 10 mg to about 1000 mg about every 12 hours, e.g., about 10 mg to about 60 mg about every 12 hours, about 60 mg to about 200 mg about every 12 hours, about 200 mg to about 500 mg about every 12 hours, about 500 mg to about 1000 mg about every 12 hours, e.g., about 15 mg about every 12 hours, about 60 mg about every 12 hours, about 120 mg about every 12 hours, about 360 mg about every 12 hours, about 700 mg about every 12 hours.

In some embodiments, the subject has been administered Compound 1, e.g., orally, once daily, e.g., about every 24 hours. In some embodiments, Compound 1 is administered, e.g., orally, to the subject at about 60 mg to about 200 mg about every 24 hours, e.g., about 90 mg about every 24 hours, about 120 mg about every 24 hours, about 150 mg about every 24 hours, about 180 mg about every 24 hours, or about 200 mg about every 24 hours.

In another aspect, the invention provides a method of treating a subject for a disorder, e.g., hereditary non-spherocytic hemolytic anemia; sickle cell anemia; thalassemia, e.g. beta-thalassemia; hereditary spherocytosis; hereditary elliptocytosis; abetalipoproteinemia; Bassen-Kornzweig syndrome; or paroxysmal nocturnal hemoglobinuria, the method comprising orally administering to the subject a dose of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg, of Compound 1.

In some embodiments, the disorder is hereditary non-spherocytic hemolytic anemia.

In some embodiments, the disorder is sickle cell anemia.

In some embodiments, the disorder is thalassemia, e.g., beta-thalassemia.

In some embodiments, the disorder is hereditary spherocytosis.

In some embodiments, the disorder is hereditary elliptocytosis.

In some embodiments, the disorder is abetalipoproteinemia.

In some embodiments, the disorder is Bassen-Kornzweig syndrome.

In some embodiments, the disorder is paroxysmal nocturnal hemoglobinuria.

In some embodiments, the method comprises administering, e.g., orally, to the subject a dose of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In some embodiments, Compound 1 is administered once or twice daily.

In some embodiments, Compound 1 is administered, e.g., orally, twice daily, e.g., about every 12 hours. In some embodiments, Compound 1 is administered to the subject at about 10 mg to about 1000 mg about every 12 hours, e.g., about 10 mg to about 60 mg about every 12 hours, about 60 mg to about 200 mg about every 12 hours, about 200 mg to about 500 mg about every 12 hours, about 500 mg to about 1000 mg about every 12 hours, e.g., about 15 mg about every 12 hours, about 60 mg about every 12 hours, about 120 mg about every 12 hours, about 360 mg about every 12 hours, about 700 mg about every 12 hours.

In some embodiments, Compound 1 is administered, e.g., orally, once daily, e.g., about every 24 hours. In some embodiments, Compound 1 is administered, e.g., orally, to the subject at about 60 mg to about 200 mg about every 24 hours, e.g., about 90 mg about every 24 hours, about 120 mg about every 24 hours, about 150 mg about every 24 hours, about 180 mg about every 24 hours, or about 200 mg about every 24 hours.

Treatment methods described herein can additionally comprise various evaluation steps prior to and/or following treatment with Compound 1.

In some embodiments, prior to and/or after treatment with Compound 1, the method further comprises the step of evaluating PK and PD parameters (e.g., plasma concentration of Compound 1, 2,3-DPG and/or ATP). This evaluation may be achieved by sample analysis of bodily fluid, such as blood by e.g., mass spectroscopy, e.g. LC-MS.

In another aspect, the invention provides an oral dosage unit of Compound 1, wherein the oral dosage unit consists of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg, of Compound 1.

In some embodiments, the oral dosage unit consists of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In another aspect, the present invention provides a method of evaluating a subject, the method comprising administering to the subject N-(4-(4-(cyclopropylmethyl)piperazine-1-carbonyl)phenyl)quinoline-8-sulfonamide (Compound 1) and acquiring information regarding the occurrence of an adverse event (AE) to thereby evaluate the subject.

In an embodiment, the adverse event is selected from headache, nausea, vomiting, and upper respiratory tract infection. In an embodiment, the adverse event is nausea. In an embodiment, the adverse event is vomiting. In an embodiment, the adverse event is upper respiratory tract infection.

In some embodiments, the subject has been administered Compound 1, e.g., orally, a dose of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg, of Compound 1.

In some embodiments, the subject has been administered Compound 1, e.g., orally, a dose of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In some embodiments, the subject has been administered, e.g., orally, Compound 1 once or twice daily.

In some embodiments, the subject has been administered Compound 1, e.g., orally, twice daily, e.g., about every 12 hours. In some embodiments, Compound 1 is administered to the subject at about 10 mg to about 1000 mg about every 12 hours, e.g., about 10 mg to about 60 mg about every 12 hours, about 60 mg to about 200 mg about every 12 hours, about 200 mg to about 500 mg about every 12 hours, about 500 mg to about 1000 mg about every 12 hours, e.g., about 15 mg about every 12 hours, about 60 mg about every 12 hours, about 120 mg about every 12 hours, about 360 mg about every 12 hours, about 700 mg about every 12 hours.

In some embodiments, the subject has been administered Compound 1, e.g., orally, once daily, e.g., about every 24 hours. In some embodiments, Compound 1 is administered, e.g., orally, to the subject at about 60 mg to about 200 mg about every 24 hours, e.g., about 90 mg about every 24 hours, about 120 mg about every 24 hours, about 150 mg about every 24 hours, about 180 mg about every 24 hours, or about 200 mg about every 24 hours.

The present invention further provides a method for increasing the lifetime of red blood cells (RBCs) in need thereof comprising contacting blood with an effective amount of (1) Compound 1 or a pharmaceutically acceptable salt thereof; (2) a composition comprising Compound 1 or a salt thereof and a carrier; or (3) a pharmaceutical composition comprising Compound 1 or a pharmaceutically acceptable salt thereof, and a pharmaceutically acceptable carrier.

In some embodiments, the method comprises orally administering to the subject a dose of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg, of Compound 1.

In some embodiments, the method comprises administering, e.g., orally, to the subject a dose of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In some embodiments, Compound 1 is administered once or twice daily.

In some embodiments, Compound 1 is administered, e.g., orally, twice daily, e.g., about every 12 hours. In some embodiments, Compound 1 is administered to the subject at about 10 mg to about 1000 mg about every 12 hours, e.g., about 10 mg to about 60 mg about every 12 hours, about 60 mg to about 200 mg about every 12 hours, about 200 mg to about 500 mg about every 12 hours, about 500 mg to about 1000 mg about every 12 hours, e.g., about 15 mg about every 12 hours, about 60 mg about every 12 hours, about 120 mg about every 12 hours, about 360 mg about every 12 hours, about 700 mg about every 12 hours.

In some embodiments, Compound 1 is administered, e.g., orally, once daily, e.g., about every 24 hours. In some embodiments, Compound 1 is administered, e.g., orally, to the subject at about 60 mg to about 200 mg about every 24 hours, e.g., about 90 mg about every 24 hours, about 120 mg about every 24 hours, about 150 mg about every 24 hours, about 180 mg about every 24 hours, or about 200 mg about every 24 hours.

The present invention further provides a method for regulating 2,3-diphosphoglycerate levels, e.g., reducing 2,3-diphosphoglycerate levels, in blood in need thereof comprising contacting blood with an effective amount of (1) Compound 1 or a pharmaceutically acceptable salt thereof; (2) a composition comprising Compound 1 or a salt thereof and a carrier; or (3) a pharmaceutical composition comprising Compound 1 or a pharmaceutically acceptable salt thereof, and a pharmaceutically acceptable carrier.

In some embodiments, the method comprises orally administering to the subject a dose of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg, of Compound 1.

In some embodiments, the method comprises administering, e.g., orally, to the subject a dose of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In some embodiments, Compound 1 is administered once or twice daily.

In some embodiments, Compound 1 is administered, e.g., orally, twice daily, e.g., about every 12 hours. In some embodiments, Compound 1 is administered to the subject at about 10 mg to about 1000 mg about every 12 hours, e.g., about 10 mg to about 60 mg about every 12 hours, about 60 mg to about 200 mg about every 12 hours, about 200 mg to about 500 mg about every 12 hours, about 500 mg to about 1000 mg about every 12 hours, e.g., about 15 mg about every 12 hours, about 60 mg about every 12 hours, about 120 mg about every 12 hours, about 360 mg about every 12 hours, about 700 mg about every 12 hours.

In some embodiments, Compound 1 is administered, e.g., orally, once daily, e.g., about every 24 hours. In some embodiments, Compound 1 is administered, e.g., orally, to the subject at about 60 mg to about 200 mg about every 24 hours, e.g., about 90 mg about every 24 hours, about 120 mg about every 24 hours, about 150 mg about every 24 hours, about 180 mg about every 24 hours, or about 200 mg about every 24 hours.

In another aspect, the present invention provides a method of treating a subject, the method comprising: administering to the subject a therapeutically effective amount of (1) Compound 1 or a pharmaceutically acceptable salt thereof; (2) a composition comprising Compound 1 or a salt thereof and a carrier; or (3) a pharmaceutical composition comprising Compound 1 or a pharmaceutically acceptable salt thereof, and a pharmaceutically acceptable carrier; and acquiring a value for the level of Compound 1, the level of 2,3-diphosphoglycerate (2,3-DPG), the level of adenosine triphosphate (ATP), or the activity of PKR in the subject, to thereby treat the subject.

In some embodiments, the method comprises orally administering to the subject a dose of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg, of Compound 1.

In some embodiments, the method comprises administering, e.g., orally, to the subject a dose of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In some embodiments, Compound 1 is administered once or twice daily.

In some embodiments, Compound 1 is administered, e.g., orally, twice daily, e.g., about every 12 hours. In some embodiments, Compound 1 is administered to the subject at about 10 mg to about 1000 mg about every 12 hours, e.g., about 10 mg to about 60 mg about every 12 hours, about 60 mg to about 200 mg about every 12 hours, about 200 mg to about 500 mg about every 12 hours, about 500 mg to about 1000 mg about every 12 hours, e.g., about 15 mg about every 12 hours, about 60 mg about every 12 hours, about 120 mg about every 12 hours, about 360 mg about every 12 hours, about 700 mg about every 12 hours.

In some embodiments, Compound 1 is administered, e.g., orally, once daily, e.g., about every 24 hours. In some embodiments, Compound 1 is administered, e.g., orally, to the subject at about 60 mg to about 200 mg about every 24 hours, e.g., about 90 mg about every 24 hours, about 120 mg about every 24 hours, about 150 mg about every 24 hours, about 180 mg about every 24 hours, or about 200 mg about every 24 hours.

In some embodiments, the value for the level of Compound 1 is acquired by analyzing the plasma concentration of Compound 1.

In some embodiments, the level of 2,3-DPG is acquired by analyzing the blood concentration of 2,3-DPG.

In some embodiments, the level of ATP is acquired by analyzing the blood concentration of ATP.

In some embodiments, the activity of PKR is acquired by analyzing the blood concentration of a $^{13}$C-label in the blood. For example, $^{13}$C-labeled glucose is administered to a subject, and incorporated into certain glycolytic intermediates in the blood.

In some embodiments, the analysis is performed by sample analysis of bodily fluid, such as blood, by e.g., mass spectroscopy, e.g. LC-MS.

In another aspect, the present invention provides a method for treating pyruvate kinase deficiency (PKD) in a subject in need thereof, comprising administering to the subject a therapeutically effective amount of (1) Compound 1 or a pharmaceutically acceptable salt thereof; (2) a composition comprising Compound 1 or a salt thereof and a carrier; or (3) a pharmaceutical composition comprising Compound 1 or a pharmaceutically acceptable salt thereof, and a pharmaceutically acceptable carrier, to thereby treat PKD in the subject.

In some embodiments, prior to, during, and/or after treatment with (1) Compound 1 or a pharmaceutically acceptable salt thereof; (2) a composition comprising Compound 1 or a salt thereof and a carrier; or (3) a pharmaceutical composition comprising Compound 1 or a pharmaceutically acceptable salt thereof, and a pharmaceutically acceptable carrier, the method further comprises the step of evaluating for levels of Compound 1, or for the levels of one or more intermediate(s) in the glycolysis pathway, e.g., evaluating for levels of one or more of 2,3-diphosphoglycerate (2,3-DPG), adenosine triphosphate (ATP), or another intermediate in the glycolysis pathway.

In some embodiments, the method comprises activating one or more isozymes of pyruvate kinase, e.g., one or more of PKR, PKM2 and/or PKL isozymes.

In some embodiments, the method comprises activating wild type PKR isozyme and/or a mutant PKR isozyme.

In some embodiments, the method comprises orally administering to the subject a dose of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg, of Compound 1.

In some embodiments, the method comprises administering, e.g., orally, to the subject a dose of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In some embodiments, Compound 1 is administered once or twice daily.

In some embodiments, Compound 1 is administered, e.g., orally, twice daily, e.g., about every 12 hours. In some embodiments, Compound 1 is administered to the subject at about 10 mg to about 1000 mg about every 12 hours, e.g., about 10 mg to about 60 mg about every 12 hours, about 60 mg to about 200 mg about every 12 hours, about 200 mg to about 500 mg about every 12 hours, about 500 mg to about 1000 mg about every 12 hours, e.g., about 15 mg about every 12 hours, about 60 mg about every 12 hours, about 120 mg about every 12 hours, about 360 mg about every 12 hours, about 700 mg about every 12 hours.

In some embodiments, Compound 1 is administered, e.g., orally, once daily, e.g., about every 24 hours. In some embodiments, Compound 1 is administered, e.g., orally, to the subject at about 60 mg to about 200 mg about every 24 hours, e.g., about 90 mg about every 24 hours, about 120 mg about every 24 hours, about 150 mg about every 24 hours, about 180 mg about every 24 hours, or about 200 mg about every 24 hours.

In another aspect, the present invention provides a method of activating pyruvate kinase in a subject in need thereof, comprising administering to the subject a therapeutically effective amount of (1) Compound 1 or a pharmaceutically acceptable salt thereof; (2) a composition comprising Compound 1 or a salt thereof and a carrier; or (3) a pharmaceutical composition comprising Compound 1 or a pharmaceutically acceptable salt thereof, and a pharmaceutically acceptable carrier, to thereby activate pyruvate kinase in the subject.

In some embodiments, the method comprises activating one or more isozymes of pyruvate kinase, e.g., one or more of PKR, PKM2 and/or PKL isozymes.

In some embodiments, the method comprises activating wild type PKR isozyme and/or a mutant PKR isozyme. In some embodiments, the mutant PKR isozyme is selected from G332S, G364D, T384M, G37E, R479H, R479K, R486W, R532W, R510Q, I90N, and R490W.

In some embodiments, the method comprises orally administering to the subject a dose of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg, of Compound 1.

In some embodiments, the method comprises administering, e.g., orally, to the subject a dose of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In some embodiments, Compound 1 is administered once or twice daily.

In some embodiments, Compound 1 is administered, e.g., orally, twice daily, e.g., about every 12 hours. In some embodiments, Compound 1 is administered to the subject at about 10 mg to about 1000 mg about every 12 hours, e.g., about 10 mg to about 60 mg about every 12 hours, about 60 mg to about 200 mg about every 12 hours, about 200 mg to about 500 mg about every 12 hours, about 500 mg to about 1000 mg about every 12 hours, e.g., about 15 mg about every 12 hours, about 60 mg about every 12 hours, about 120 mg about every 12 hours, about 360 mg about every 12 hours, about 700 mg about every 12 hours.

In some embodiments, Compound 1 is administered, e.g., orally, once daily, e.g., about every 24 hours. In some embodiments, Compound 1 is administered, e.g., orally, to the subject at about 60 mg to about 200 mg about every 24 hours, e.g., about 90 mg about every 24 hours, about 120 mg about every 24 hours, about 150 mg about every 24 hours, about 180 mg about every 24 hours, or about 200 mg about every 24 hours.

The present invention further provides a method for treating hereditary non-spherocytic hemolytic anemia comprising administering to a subject in need thereof a therapeutically effective amount of (1) Compound 1 or a pharmaceutically acceptable salt thereof; (2) a composition comprising Compound 1 or a salt thereof and a carrier; or (3) a pharmaceutical composition comprising Compound 1 or a pharmaceutically acceptable salt thereof, and a pharmaceutically acceptable carrier.

In some embodiments, prior to, during, and/or after treatment with (1) Compound 1 or a pharmaceutically acceptable salt thereof; (2) a composition comprising Compound 1 or a salt thereof and a carrier; or (3) a pharmaceutical composition comprising Compound 1 or a pharmaceutically acceptable salt thereof, and a pharmaceutically acceptable carrier, the method further comprises the step of evaluating for the level of Compound 1, or for the levels of one or more intermediate(s) in the glycolysis pathway, e.g., evaluating for levels of one or more of 2,3-diphosphoglycerate (2,3-DPG), adenosine triphosphate (ATP), or another intermediate in the glycolysis pathway.

In some embodiments, the method comprises orally administering to the subject a dose of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg, of Compound 1.

In some embodiments, the method comprises administering, e.g., orally, to the subject a dose of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In some embodiments, Compound 1 is administered once or twice daily.

In some embodiments, Compound 1 is administered, e.g., orally, twice daily, e.g., about every 12 hours. In some embodiments, Compound 1 is administered to the subject at about 10 mg to about 1000 mg about every 12 hours, e.g., about 10 mg to about 60 mg about every 12 hours, about 60 mg to about 200 mg about every 12 hours, about 200 mg to about 500 mg about every 12 hours, about 500 mg to about 1000 mg about every 12 hours, e.g., about 15 mg about every 12 hours, about 60 mg about every 12 hours, about 120 mg about every 12 hours, about 360 mg about every 12 hours, about 700 mg about every 12 hours.

In some embodiments, Compound 1 is administered, e.g., orally, once daily, e.g., about every 24 hours. In some embodiments, Compound 1 is administered, e.g., orally, to the subject at about 60 mg to about 200 mg about every 24 hours, e.g., about 90 mg about every 24 hours, about 120 mg about every 24 hours, about 150 mg about every 24 hours, about 180 mg about every 24 hours, or about 200 mg about every 24 hours.

The present invention further provides a method for treating sickle cell anemia comprising administering to a subject in need thereof a therapeutically effective amount of (1) Compound 1 or a pharmaceutically acceptable salt thereof; (2) a composition comprising Compound 1 or a salt thereof and a carrier; or (3) a pharmaceutical composition comprising Compound 1 or a pharmaceutically acceptable salt thereof, and a pharmaceutically acceptable carrier.

In some embodiments, prior to, during, and/or after treatment with (1) Compound 1 or a pharmaceutically acceptable salt thereof; (2) a composition comprising Compound 1 or a salt thereof and a carrier; or (3) a pharmaceutical composition comprising Compound 1 or a pharmaceutically acceptable salt thereof, and a pharmaceutically acceptable carrier, the method further comprises the step of evaluating for the level of Compound 1, or for the levels of one or more intermediate(s) in the glycolysis pathway, e.g., evaluating for levels of one or more of 2,3-diphosphoglycerate (2,3-DPG), adenosine triphosphate (ATP), or another intermediate in the glycolysis pathway.

In some embodiments, the method comprises orally administering to the subject a dose of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg, of Compound 1.

In some embodiments, the method comprises administering, e.g., orally, to the subject a dose of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In some embodiments, Compound 1 is administered once or twice daily.

In some embodiments, Compound 1 is administered, e.g., orally, twice daily, e.g., about every 12 hours. In some embodiments, Compound 1 is administered to the subject at about 10 mg to about 1000 mg about every 12 hours, e.g., about 10 mg to about 60 mg about every 12 hours, about 60 mg to about 200 mg about every 12 hours, about 200 mg to about 500 mg about every 12 hours, about 500 mg to about 1000 mg about every 12 hours, e.g., about 15 mg about every 12 hours, about 60 mg about every 12 hours, about 120 mg about every 12 hours, about 360 mg about every 12 hours, about 700 mg about every 12 hours.

In some embodiments, Compound 1 is administered, e.g., orally, once daily, e.g., about every 24 hours. In some embodiments, Compound 1 is administered, e.g., orally, to the subject at about 60 mg to about 200 mg about every 24 hours, e.g., about 90 mg about every 24 hours, about 120 mg about every 24 hours, about 150 mg about every 24 hours, about 180 mg about every 24 hours, or about 200 mg about every 24 hours.

The present invention further provides a method for treating hemolytic anemia (e.g., chronic hemolytic anemia caused by phosphoglycerate kinase deficiency, Blood Cells Mol Dis, 2011; 46(3):206) comprising administering to a subject in need thereof a therapeutically effective amount of (1) Compound 1 or a pharmaceutically acceptable salt thereof; (2) a composition comprising Compound 1 or a salt thereof and a carrier; or (3) a pharmaceutical composition comprising Compound 1 or a pharmaceutically acceptable salt thereof, and a pharmaceutically acceptable carrier.

In some embodiments, prior to, during, and/or after treatment with (1) Compound 1 or a pharmaceutically acceptable salt thereof; (2) a composition comprising Compound 1 or a salt thereof and a carrier; or (3) a pharmaceutical composition comprising Compound 1 or a pharmaceutically acceptable salt thereof, and a pharmaceutically acceptable carrier, the method further comprises the step of evaluating for the level of Compound 1, or for the levels of one or more intermediate(s) in the glycolysis pathway, e.g., evaluating for levels of one or more of 2,3-diphosphoglycerate (2,3-DPG), adenosine triphosphate (ATP), or another intermediate in the glycolysis pathway.

In some embodiments, the method comprises orally administering to the subject a dose of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg, of Compound 1.

In some embodiments, the method comprises administering, e.g., orally, to the subject a dose of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In some embodiments, Compound 1 is administered once or twice daily.

In some embodiments, Compound 1 is administered, e.g., orally, twice daily, e.g., about every 12 hours. In some embodiments, Compound 1 is administered to the subject at about 10 mg to about 1000 mg about every 12 hours, e.g., about 10 mg to about 60 mg about every 12 hours, about 60 mg to about 200 mg about every 12 hours, about 200 mg to about 500 mg about every 12 hours, about 500 mg to about 1000 mg about every 12 hours, e.g., about 15 mg about every 12 hours, about 60 mg about every 12 hours, about 120 mg about every 12 hours, about 360 mg about every 12 hours, about 700 mg about every 12 hours.

In some embodiments, Compound 1 is administered, e.g., orally, once daily, e.g., about every 24 hours. In some embodiments, Compound 1 is administered, e.g., orally, to the subject at about 60 mg to about 200 mg about every 24 hours, e.g., about 90 mg about every 24 hours, about 120 mg about every 24 hours, about 150 mg about every 24 hours, about 180 mg about every 24 hours.

The present invention further provides a method for treating thalassemia (e.g., beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases comprising administering to a subject in need thereof a therapeutically effective amount of (1) N-(4-(4-(cyclopropylmethyl)piperazine-1-carbonyl)phenyl)quinoline-8-sulfonamide (Compound 1) or a pharmaceutically acceptable salt thereof; (2) a composition comprising Compound 1 or a salt thereof and a carrier; or (3) a pharmaceutical composition comprising Compound 1 or a pharmaceutically acceptable salt thereof, and a pharmaceutically acceptable carrier.

In some embodiments, prior to, during, and/or after treatment with (1) Compound 1 or a pharmaceutically acceptable salt thereof; (2) a composition comprising Compound 1 or a salt thereof and a carrier; or (3) a pharmaceutical composition comprising Compound 1 or a pharmaceutically acceptable salt thereof, and a pharmaceutically acceptable carrier, the method further comprises the step of evaluating for the level of Compound 1, or for the levels of one or more intermediate(s) in the glycolysis pathway, e.g., evaluating for levels of one or more of 2,3-diphosphoglycerate (2,3-DPG), adenosine triphosphate (ATP), or another intermediate in the glycolysis pathway.

In some embodiments, the method comprises orally administering to the subject a dose of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg, of Compound 1.

In some embodiments, the method comprises administering, e.g., orally, to the subject a dose of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In some embodiments, Compound 1 is administered once or twice daily.

In some embodiments, Compound 1 is administered, e.g., orally, twice daily, e.g., about every 12 hours. In some embodiments, Compound 1 is administered to the subject at about 10 mg to about 1000 mg about every 12 hours, e.g., about 10 mg to about 60 mg about every 12 hours, about 60 mg to about 200 mg about every 12 hours, about 200 mg to about 500 mg about every 12 hours, about 500 mg to about 1000 mg about every 12 hours, e.g., about 15 mg about every 12 hours, about 60 mg about every 12 hours, about 120 mg about every 12 hours, about 360 mg about every 12 hours, about 700 mg about every 12 hours.

In some embodiments, Compound 1 is administered, e.g., orally, once daily, e.g., about every 24 hours. In some embodiments, Compound 1 is administered, e.g., orally, to the subject at about 60 mg to about 200 mg about every 24 hours, e.g., about 90 mg about every 24 hours, about 120 mg about every 24 hours, about 150 mg about every 24 hours, about 180 mg about every 24 hours.

The present invention further provides a method for treating diseases or conditions that are associated with increased 2,3-diphosphoglycerate levels (e.g., liver diseases (*Am J Gastroenterol,* 1987; 82(12):1283) and Parkinson's (*J. Neurol,* Neurosurg, and Psychiatry 1976, 39:952) comprising administering to a subject in need thereof a therapeutically effective amount of (1) Compound 1 or a pharmaceutically acceptable salt thereof; (2) a composition comprising Compound 1 or a salt thereof and a carrier; or (3) a pharmaceutical composition comprising Compound 1 or a pharmaceutically acceptable salt thereof, and a pharmaceutically acceptable carrier.

In some embodiments, the method comprises orally administering to the subject a dose of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg, of Compound 1.

In some embodiments, the method comprises administering, e.g., orally, to the subject a dose of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In some embodiments, Compound 1 is administered once or twice daily.

In some embodiments, Compound 1 is administered, e.g., orally, twice daily, e.g., about every 12 hours. In some embodiments, Compound 1 is administered to the subject at about 10 mg to about 1000 mg about every 12 hours, e.g., about 10 mg to about 60 mg about every 12 hours, about 60 mg to about 200 mg about every 12 hours, about 200 mg to about 500 mg about every 12 hours, about 500 mg to about 1000 mg about every 12 hours, e.g., about 15 mg about every 12 hours, about 60 mg about every 12 hours, about 120 mg about every 12 hours, about 360 mg about every 12 hours, about 700 mg about every 12 hours.

In some embodiments, Compound 1 is administered, e.g., orally, once daily, e.g., about every 24 hours. In some embodiments, Compound 1 is administered, e.g., orally, to the subject at about 60 mg to about 200 mg about every 24 hours, e.g., about 90 mg about every 24 hours, about 120 mg about every 24 hours, about 150 mg about every 24 hours, about 180 mg about every 24 hours.

A compound N-(4-(4-(cyclopropylmethyl)piperazine-1-carbonyl)phenyl)quinoline-8-sulfonamide (Compound 1) and compositions comprising Compound 1 described herein are allosteric activators of PKR mutants and isoforms having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, G37E, R479H, R479K, R486W, R532W, R510Q, 190N, and R490W. Without being bound by theory, Compound 1 affects the activities of PKR mutants by activating FBP non-responsive PKR mutants, restoring thermostability to mutants with decreased stability, or restoring catalytic efficiency to impaired mutants. Compound 1 is also an activator of wild type PKR.

In an embodiment, to increase the lifetime of the red blood cells, N-(4-(4-(cyclopropylmethyl)piperazine-1-carbonyl)phenyl)quinoline-8-sulfonamide (Compound 1), composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes). Without being bound by theory, Compound 1 increases the lifetime of the RBCs, thus counteract aging of stored blood, by impacting the rate of release of 2,3-DPG from the blood. A decrease in the level of 2,3-DPG concentration induces a leftward shift of the oxygen-hemoglobin dissociation curve and shifts the allosteric equilibribrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, Compound 1 is useful as an antisickling agent. In another embodiment, to regulate 2,3-diphosphoglycerate, e.g. reduce 2,3-diphosphoglycerate levels, Compound 1 is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes).

BRIEF DESCRIPTION OF THE DRAWINGS

FIG. 4 depicts a summary of the number of subjects experiencing adverse events (AEs) by treatment group in the SAD study, including the safety analysis set of both fed and fasted periods.

FIG. 6 depicts the pharmacokinetic (PK) parameter values of a compound N-(4-(4-(cyclopropylmethyl)piperazine-1-carbonyl)phenyl)quinoline-8-sulfonamide Compound 1 following a single oral dose (SAD study).

DETAILED DESCRIPTION OF THE INVENTION

Figure 1:
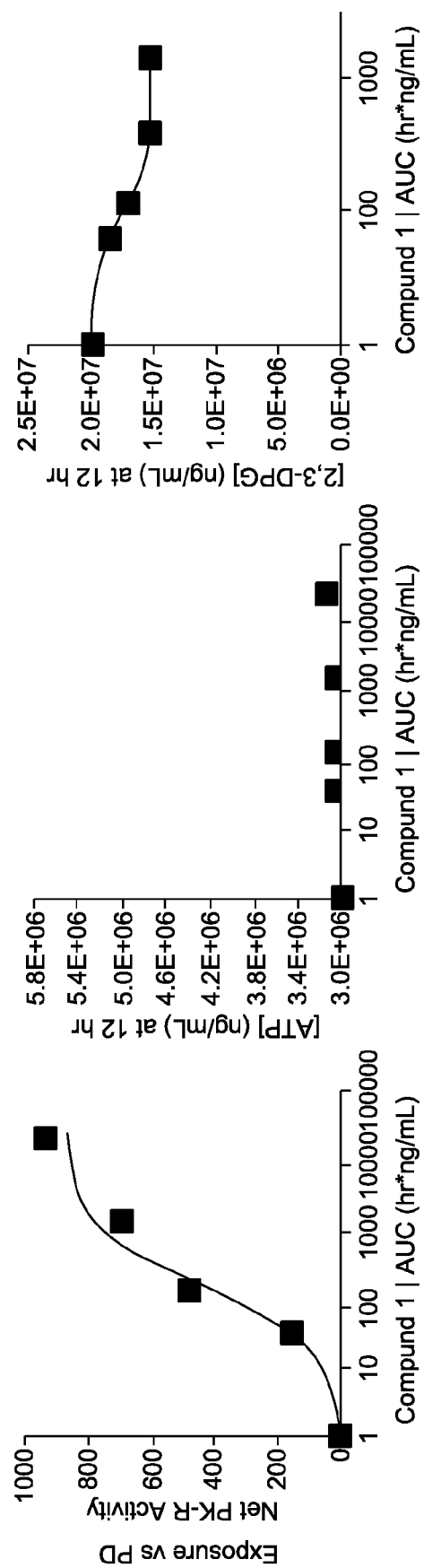
FIG. 1 depicts line graphs showing PKR activity (left), ATP levels (center), and 2,3-DPG levels (right) in whole blood from C57/BL6 mice treated with a single dose of a compound N-(4-(4-(cyclopropylmethyl)piperazine-1-carbonyl)phenyl)quinoline-8-sulfonamide (Compound 1) at four dose levels (1 mpk, 10 mpk, 50 mpk, and 150 mpk). Top row: Raw data for PKR activity, ATP level, and 2,3-DPG level assesments; Center row: Percent changes of each marker for each dose normalized to vehicle treated; Bottom row: Pharmacokinetic/pharmacodynamic correlation between Compound 1 exposure in plasma and each marker.

The details of construction and the arrangement of components set forth in the following description or illustrated in the drawings are not meant to be limiting. Embodiments can be practiced or carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

As used herein, the term "treat" means decrease, suppress, attenuate, diminish, arrest, or stabilize the development or progression of a disease/disorder (e.g., hereditary non-spherocytic hemolytic anemia; sickle cell anemia; thalassemia, e.g. beta-thalassemia; hereditary spherocytosis; hereditary elliptocytosis; sbetalipoproteinemia; Bassen-Kornzweig syndrome; or paroxysmal nocturnal hemoglobinuria), lessen the severity of the disease/disorder (e.g., hereditary non-spherocytic hemolytic anemia; sickle cell anemia; thalassemia, e.g. beta-thalassemia; hereditary spherocytosis; hereditary elliptocytosis; sbetalipoproteinemia; Bassen-Kornzweig syndrome; or paroxysmal nocturnal hemoglobinuria) or improve the symptoms associated with the disease/disorder (e.g., e.g., hereditary non-spherocytic hemolytic anemia; sickle cell anemia; thalassemia, e.g. beta-thalassemia; hereditary spherocytosis; hereditary elliptocytosis; sbetalipoproteinemia; Bassen-Kornzweig syndrome; or paroxysmal nocturnal hemoglobinuria).

As used herein, an amount of a compound N-(4-(4-(cyclopropylmethyl)piperazine-1-carbonyl)phenyl)quinoline-8-sulfonamide (Compound 1) effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, the dosing amount refers to the free base of Compound 1 or a pharmaceutically acceptable salt or solvate (e.g., hydrate) thereof.

As used herein, the term "subject" is intended to mean human. Exemplary human subjects include a human patient (referred to as a patient) having a disorder, e.g., a disorder described herein or a normal subject.

As used herein, the term "acquire" or "acquiring" as the terms are used herein, refer to obtaining possession of a physical entity (e.g., a sample, e.g., blood sample or blood plasma sample), or a value, e.g., a numerical value, by "directly acquiring" or "indirectly acquiring" the physical entity or value. "Directly acquiring" means performing a process (e.g., an analytical method) to obtain the physical entity or value. "Indirectly acquiring" refers to receiving the physical entity or value from another party or source (e.g., a third party laboratory that directly acquired the physical entity or value). Directly acquiring a value includes performing a process that includes a physical change in a sample or another substance, e.g., performing an analytical process which includes a physical change in a substance, e.g., a sample, performing an analytical method, e.g., a method as described herein, e.g., by sample analysis of bodily fluid, such as blood by, e.g., mass spectroscopy, e.g. LC-MS.

Methods of Treatment

In one embodiment, provided is a method for treating or preventing a disease, condition or disorder as described herein (e.g., treating) comprising administering to a subject in need thereof N-(4-(4-(cyclopropylmethyl)piperazine-1-carbonyl)phenyl)quinoline-8-sulfonamide (Compound 1).

In some embodiments, the disorder is selected from hereditary non-spherocytic hemolytic anemia; sickle cell anemia; thalassemia, e.g. beta-thalassemia; hereditary spherocytosis; hereditary elliptocytosis; sbetalipoproteinemia; Bassen-Kornzweig syndrome; or paroxysmal nocturnal hemoglobinuria.

N-(4-(4-(cyclopropylmethyl)piperazine-1-carbonyl)phenyl)quinoline-8-sulfonamide (Compound 1) and compositions described herein can be administered to cells in culture, e.g. in vitro or ex vivo, or to a subject, e.g., in vivo, to treat, prevent, and/or diagnose a variety of disorders, including those described herein below.

Compositions and Routes of Administration

The compositions delineated herein include the compound N-(4-(4-(cyclopropylmethyl)piperazine-1-carbonyl)phenyl)quinoline-8-sulfonamide (Compound 1), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with Compound 1, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

In some embodiments, Compound 1 is orally administering to the subject at a dose of about 10 mg to about 3000 mg, e.g., about 10 mg to about 60 mg, about 60 mg to about 200 mg, about 200 mg to about 500 mg, about 500 mg to about 1200 mg, about 1200 mg to about 2000 mg, or about 2000 mg to about 3000 mg, e.g., about 30 mg, about 120 mg, about 360 mg, about 700 mg, about 1400 mg, about 2500 mg.

In some embodiments, the method comprises administering, e.g., orally, to the subject a dose of about 50 mg to about 300 mg, e.g., about 50 mg, about 75 mg, about 100 mg, about 125 mg, about 150 mg, about 175 mg, 200 mg, about 225 mg, about 250 mg, about 275 mg, about 300 mg, of Compound 1.

In some embodiments, Compound 1 is administered once or twice daily.

In some embodiments, Compound 1 is administered, e.g., orally, twice daily, e.g., about every 12 hours. In some embodiments, Compound 1 is administered to the subject at about 10 mg to about 1000 mg about every 12 hours, e.g., about 10 mg to about 60 mg about every 12 hours, about 60 mg to about 200 mg about every 12 hours, about 200 mg to about 500 mg about every 12 hours, about 500 mg to about 1000 mg about every 12 hours, e.g., about 15 mg about every 12 hours, about 60 mg about every 12 hours, about 120 mg about every 12 hours, about 360 mg about every 12 hours, about 700 mg about every 12 hours.

In some embodiments, Compound 1 is administered, e.g., orally, once daily, e.g., about every 24 hours. In some embodiments, Compound 1 is administered, e.g., orally, to the subject at about 60 mg to about 200 mg about every 24 hours, e.g., about 90 mg about every 24 hours, about 120 mg about every 24 hours, about 150 mg about every 24 hours, about 180 mg about every 24 hours.

When the compositions provided herewith comprise a combination of Compound 1 and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with Compound 1 in a single composition.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compound N-(4-(4-(cyclopropylmethyl)piperazine-1-carbonyl)phenyl)quinoline-8-sulfonamide (Compound 1) can activate wild type PKR and/or mutant PKRs. Some examples of the mutants that are activated by the compounds described herein include G332S, G364D, T384M, G37E, R479H, R479K, R486W, R532W, R510Q, 190N, and R490W. Accordingly, a patient and/or subject can be selected for treatment using Compound 1 by first evaluating the patient and/or subject to determine whether the subject carries a mutation in PKR (for examples, one of the mutations as described herein), and if the subject is determined to be carrying a mutation in PKR thus is in need of activation of the activity of the mutant PKR, then optionally administering to the subject Compound 1. A subject can be evaluated as carrying a mutation in PKR using methods known in the art. The subject can also be monitored, for example, subsequent to administration of Compound 1. In embodiments, the subject can be monitored for evaluation of certain PK/PD parameters of Compound 1 such as levels of Compound 1, levels of 2,3-DPG, or levels of ATP.

EXAMPLES

Example 1. Synthesis of N-(4-(4-(cyclopropylmethyl)piperazine-1-carbonyl)phenyl)quinoline-8-sulfonamide (Compound 1)

The synthesis of Compound 1 was carried out following the procedure described in U.S. Pat. No. 8,785,450, which is incorporated herein by reference in its entirety.

Example 2. N-(4-(4-(cyclopropylmethyl)piperazine-1-carbonyl)phenyl)quinoline-8-sulfonamide (Compound 1) Activation of Pyruvate Kinase In Vivo Enhances Red Cell Glycolysis in Mice Pyruvate kinase deficiency (PKD) is an autosomal recessive enzymopathy that is the most common cause of hereditary nonspherocytic hemolytic anemia (HNSHA). PKD is a rare disease characterized by a life-long chronic hemolysis with severe co-morbidities. It is hypothesized that insufficient energy production to maintain red cell membrane homeostasis promotes the chronic hemolysis. Treatment is generally palliative, focusing on the resultant anemia, and there are no approved drugs that directly target mutated pyruvate kinase.

Compound 1 is an allosteric activator of the red cell isoform of pyruvate kinase (PKR) that has recently entered Phase I clinical trials in normal healthy volunteers. Compound 1 increases the catalytic efficiency and enhances the protein stability of a spectrum of recombinantly expressed PKR mutant proteins that have been associated with PKD. PKD red cells are characterized by changes in metabolism associated with defective glycolysis, including a build-up of the upstream glycolytic intermediate 2,3-DPG and deficiency in the PKR product adenosine triphosphate (ATP). PKR flux, e.g. the rate of carbon flow through the PKR enzyme reaction, was examined in PKD patient or WT donor blood samples by incubation of whole blood with a stable isotope tracer, [U-$^{13}$C6]-glucose. At various time points after the addition of [U-$^{13}$C6]-glucose, metabolism was quenched and metabolites were extracted. Metabolite pool sizes and $^{13}$C label incorporation into glycolytic intermediates were monitored by LC/MS. The rate of label incorporation was found to be significantly slower in PKD patient red cells, consistent with decreased glycolytic activity. Treatment of PKD red cells with Compound 1 ex-vivo induces changes in metabolism consistent with increased glycolytic activity including reduced 2,3-DPG levels, increased ATP levels, and increased PKR enzyme activity levels.

Figure 2:
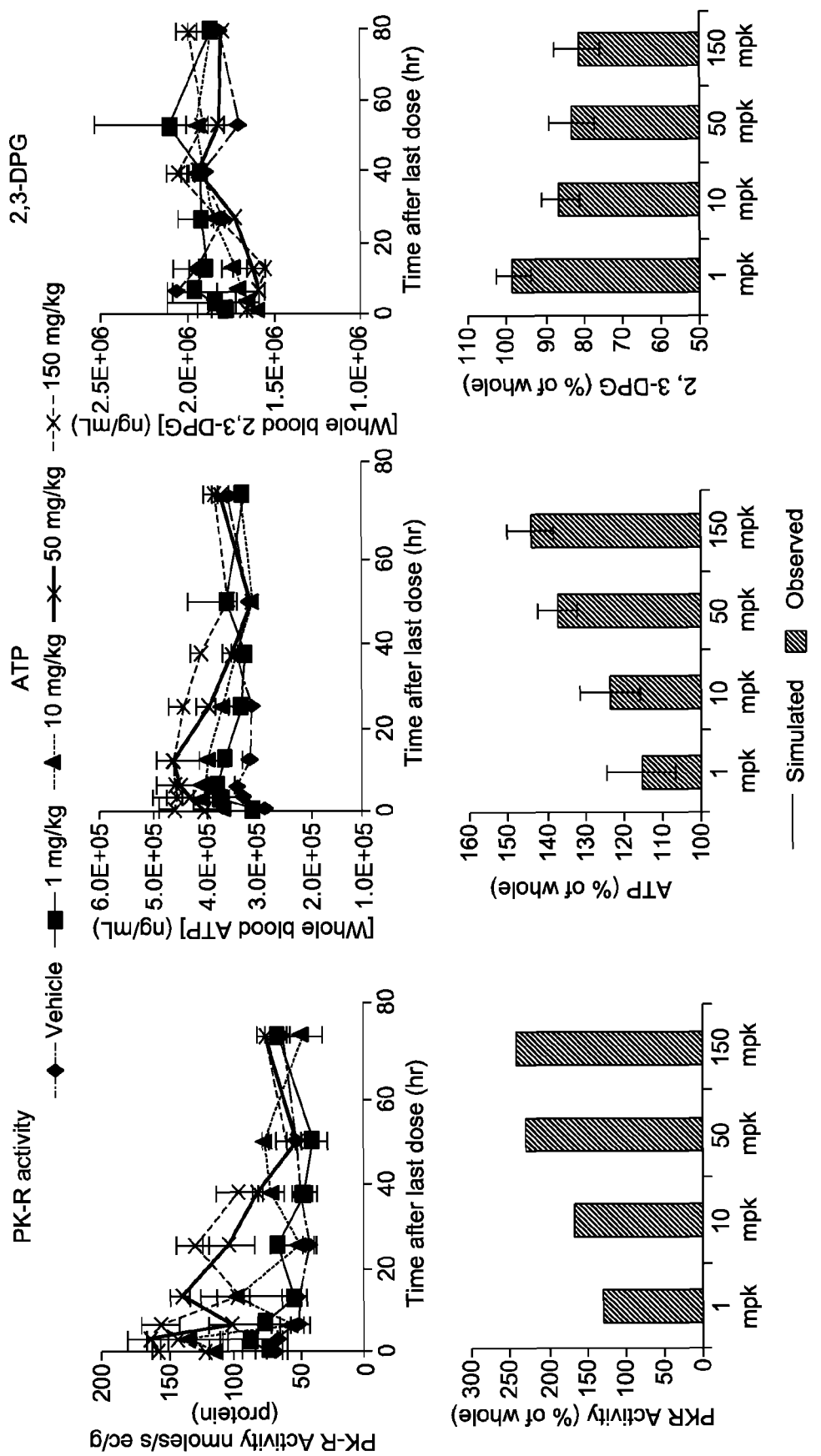
FIG. 2 depicts line graphs showing PKR activity (left), ATP levels (center), and 2,3-DPG levels (right) in whole blood from C57/BL6 mice treated with a multiple doses (13 doses, BID) of a compound N-(4-(4-(cyclopropylmethyl)piperazine-1-carbonyl)phenyl)quinoline-8-sulfonamide (Compound 1) at four dose levels (1 mpk, 10 mpk, 50 mpk, and 150 mpk). Top row: Raw data for PKR activity, ATP level, and 2,3-DPG level assesments; Center row: Percent changes of each marker for each dose normalized to vehicle treated; Bottom row: Pharmacokinetic/pharmacodynamic correlation between Compound 1 exposure in plasma and each marker.
Figure 2:
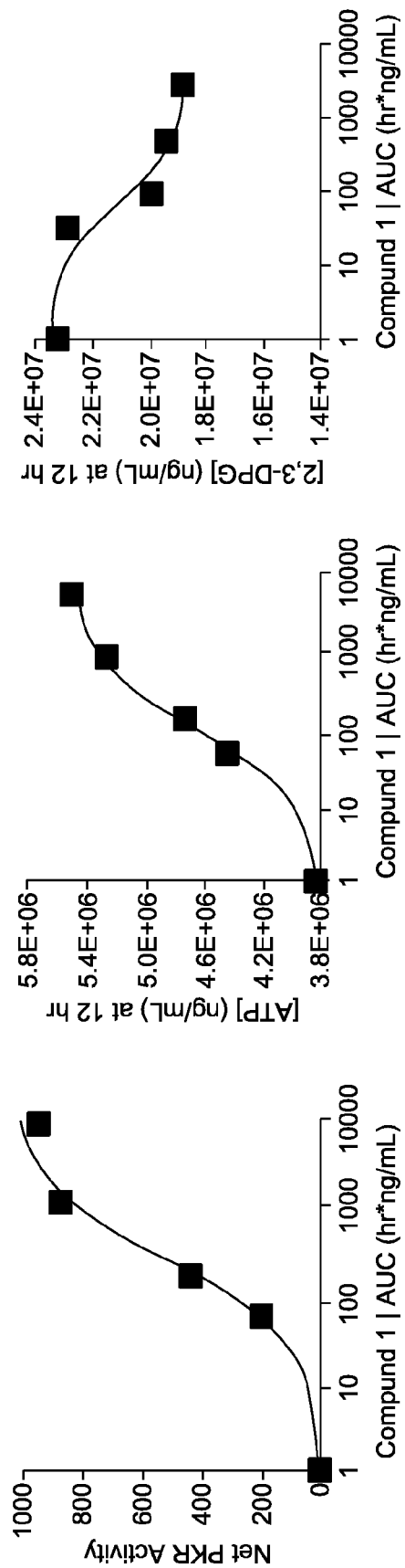

The effect of Compound 1 on red cell metabolism in vivo was evaluated in mice. C57/BL6 mice were dosed by oral gavage either with a single dose, or with multiple doses (13 doses, BID) of Compound 1 for 7 days. Dose levels tested were 1 mpk, 10 mpk, 50 mpk, and 150 mpk. Following the last dose, mice were bled to evaluate drug exposure and pharmacodynamic markers including 2,3-DPG and ATP levels, and PKR activity. Compound 1 was demonstrated to be a well-behaved compound, with dose-proportional increase in exposure, both in the single dose and multiple dose studies. A single dose of Compound 1 resulted in a dose-dependent increase in PKR activity levels (FIG. 1, left), concomitant with reduction in 2,3-DPG levels (FIG. 1, right). There were no significant changes in ATP levels after a single administration of Compound 1 (FIG. 1, center). In the multiple dose studies, similar changes in PKR activity (FIG. 2, left) and 2,3-DPG levels were observed (FIG. 2, right). In contrast to the single-dose study, ATP levels in the multiple dose study were observed to be robustly increased in a dose-dependent manner (FIG. 2, center). The resulting pharmacokinetic/pharmacodynamic correlations between Compound 1 exposure in plasma and each pharmacodynamic marker (PKR activity as well as ATP and 2,3-DPG levels) for both the single dose and multiple dose studies further highlights these observations (FIGS. 1 and 2, lower panels).

Figure 3A:
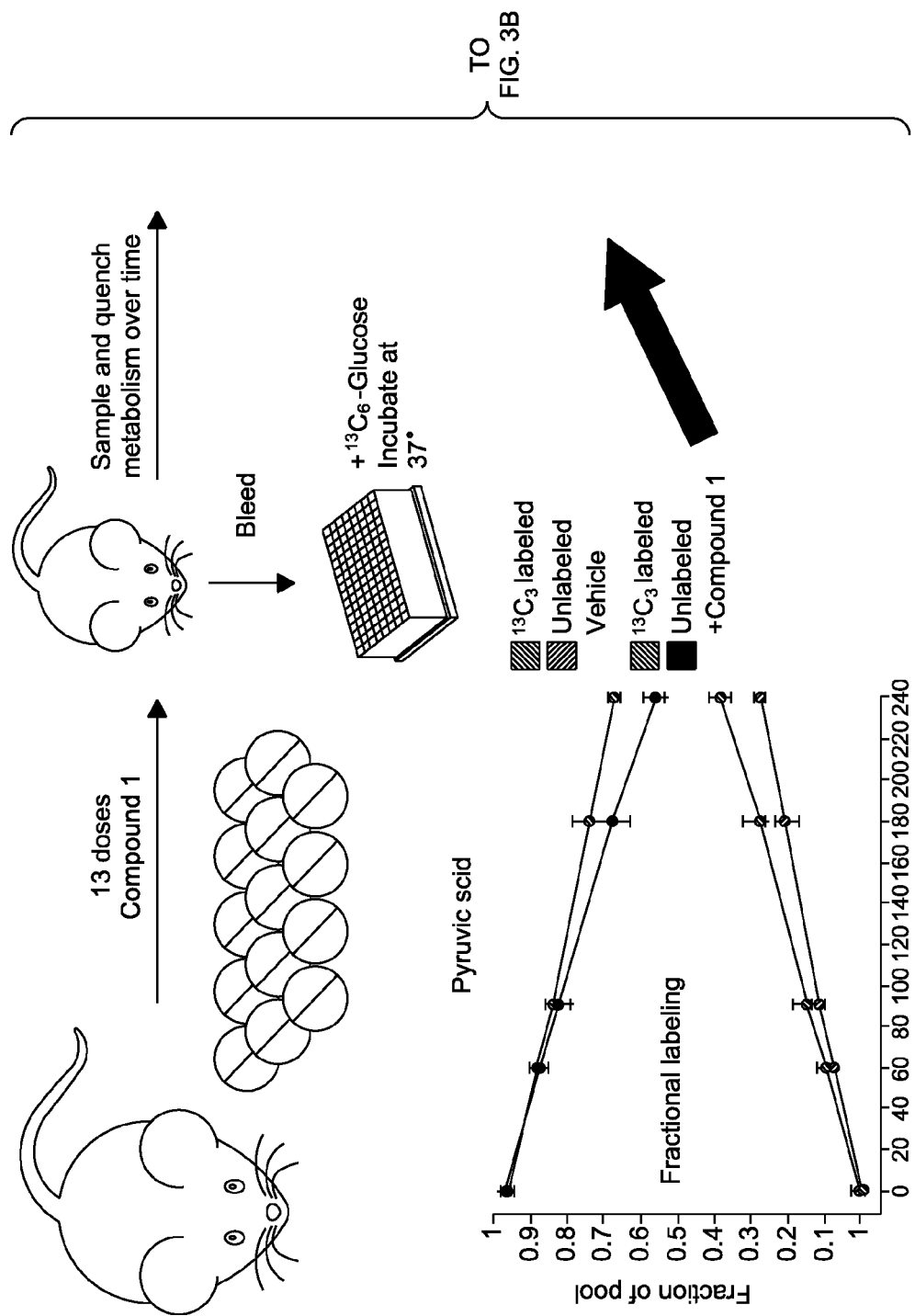
FIG. 3 depicts a schematic for the determination of PK flux activity in mice. C57/BL6 mice are administered 13 doses (BID) of a compound N-(4-(4-(cyclopropylmethyl)piperazine-1-carbonyl)phenyl)quinoline-8-sulfonamide (Compound 1, 100 mpk), and whole blood samples are removed over time. The blood samples are immediately incubated at 37° C. in the presence of [U-$^{13}$C6]-glucose, and the metabolites are extracted and quantified. The resulting data are subjected to a kinetic flux model to determine the overall change in carbon flow through the PKR reaction.
Figure 3B:
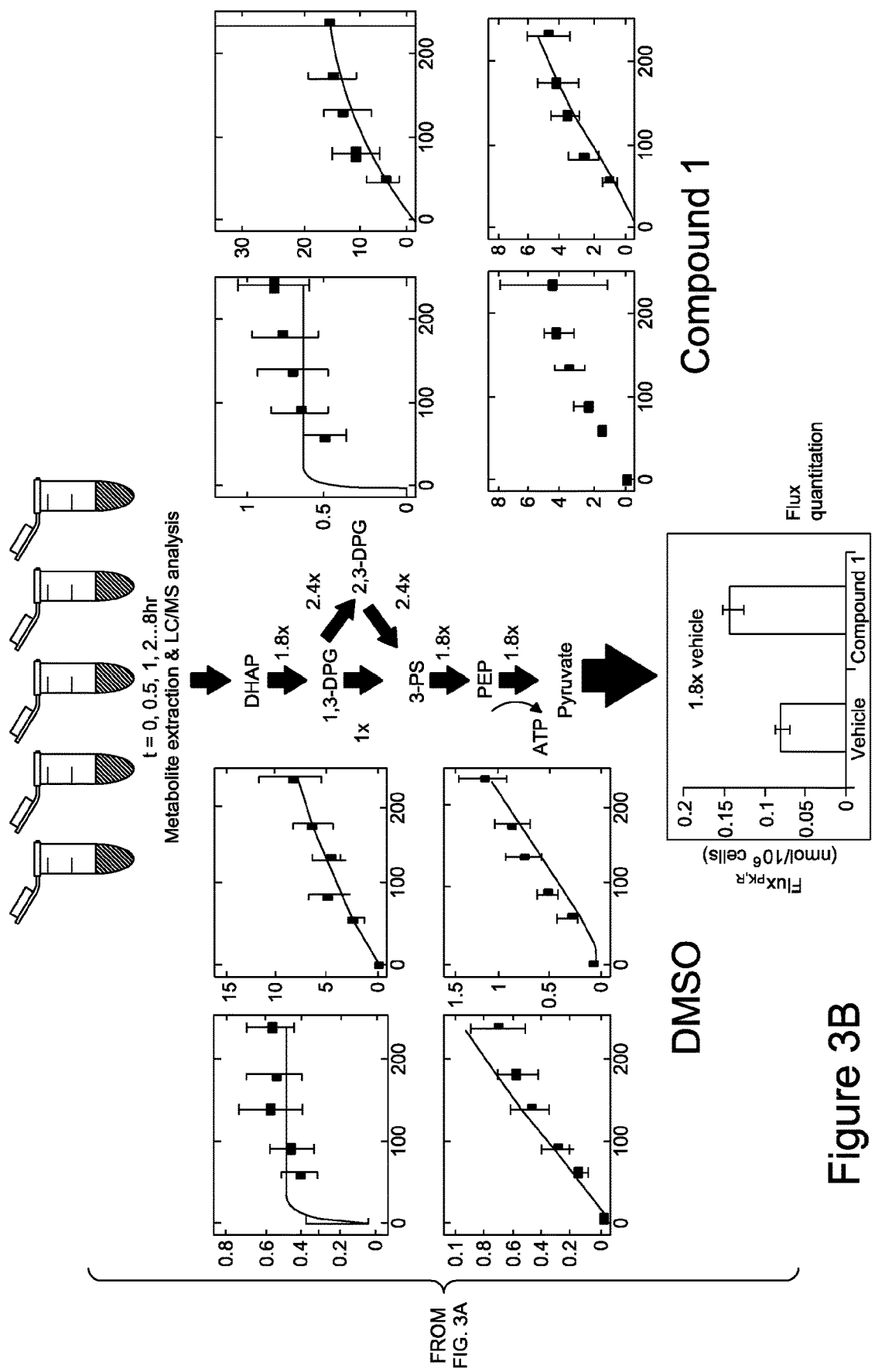

The effect of Compound 1 on PKR flux was assessed in whole blood from mice treated with Compound 1. C57BL/6 mice were dosed by oral gavage with Compound 1 at 100 mpk BID for 13 total doses. Whole blood was incubated with [U-$^{13}$C6]-glucose at 37° C. and the metabolite pool sizes and rate of $^{13}$C label incorporation into glycolytic intermediates were assessed. The data were subsequently analyzed using a mathematical kinetic flux model to quantify the overall change in carbon flow through the PKR reaction. Using this model, it was determined that Compound 1 treatment significantly increased glycolytic flux through the PKR reaction as depicted schematically in FIG. 3.

Collectively, these data demonstrate that Compound 1 not only potently binds to and activates the PKR enzyme in vivo, but this enzyme activation induces enhanced glycolytic pathway activity in red cells that results in profound changes in cellular metabolism, as reflected in dramatically increased ATP levels and reduced 2,3-DPG levels. As Compound 1 has similar potency against the WT PKR enzyme as against tested mutant PKR enzymes in vitro, these data support the hypothesis that Compound 1 treatment may similarly enhance glycolytic activity in PKD patients and thus correct the underlying pathology of PKD.

Example 3. Clinical Studies of the Safety, Tolerability, Pharmacokinetics (PK) and Pharmacodynamics (PD) of a Pyruvate Kinase-R Activator in Healthy Subjects Compound 1 is a novel, first-in-class, small molecule allosteric activator of PK-R that directly targets the underlying metabolic defect in PKD. Pre-clinical studies demonstrated that Compound 1 increases the activity of both wild type and various mutated PK-R enzymes. The key objective of these first-in-human, Phase I, randomized, double-blind, placebo-controlled single and multiple ascending dose studies (SAD and MAD) are to identify a safe and pharmacodynamically active dose and schedule for Compound 1 to be used in subsequent clinical studies in subjects with pyruvate kinase deficiency.

Methods

In the single ascending dose (SAD) study, healthy men and women (non-childbearing potential) aged 18-60 years were randomized to receive a single oral dose of Compound 1 or placebo (P). Key exclusion criteria included glucose 6-phosphate dehydrogenase deficiency, blood donation, blood loss of greater than 500 mL, or transfusion of blood or plasma within three months of screening. Six cohorts were evaluated, each containing 8 subjects (6 subjects receiving Compound 1, 2 subjects receiving placebo (P)), starting with 30 mg in cohort 1 followed by 120 mg, 360 mg, 700 mg, 1400 mg and 2500 mg in cohorts 2-6, respectively.

In the multiple ascending dose (MAD) study, 2 cohorts (120 mg BID and 360 mg BID) of 8 subjects each (6 subjects receiving Compound 1, 2 subjects receiving placebo (P)) have completed 14 days of dosing and 2 weeks of follow-up. In both studies, safety assessments included adverse events (AEs), vital signs, ECG and clinical laboratory parameters. Serial blood samples were drawn for assessment of PK and PD parameters (2,3-DPG and ATP) pre-dose and at regular intervals thereafter at multiple doses in both the SAD and MAD studies. Specifically, plasma concentrations of Compound 1 and blood concentrations of 2,3-DPG and ATP were analyzed by tandem mass spectrometry methods.

The MAD study was completed by assessing safety, tolerability, and pharmacokinetics/pharmacodynamics (PK/PD) of Compound 1 in healthy volunteers and to identify a dosing schedule for future trials in patients with PK deficiency. A phase 1, single-center, randomized, double-blind, placebo-controlled MAD study (ClinicalTrials.gov NCT02149966) was conducted in healthy men and women (18-60 years), in 6 sequential cohorts (each cohort: n=6 Compound 1, n=2 placebo). Subjects received twice daily oral doses of Compound 1 at 15 mg to 700 mg (q12h), or 120 mg once daily (q24 hr) for 14 days with follow-up to Day 29. Adverse events (AEs), laboratory parameters, ECGs, and vital signs were monitored. Plasma concentrations of Compound 1 and whole blood 2,3-DPG and ATP levels were measured in serial blood samples for PK/PD assessment. Hormone levels were monitored due to pre-clinical data suggesting potential modulation.

Results

Single Ascending Dose (SAD) Study

Figure 5:
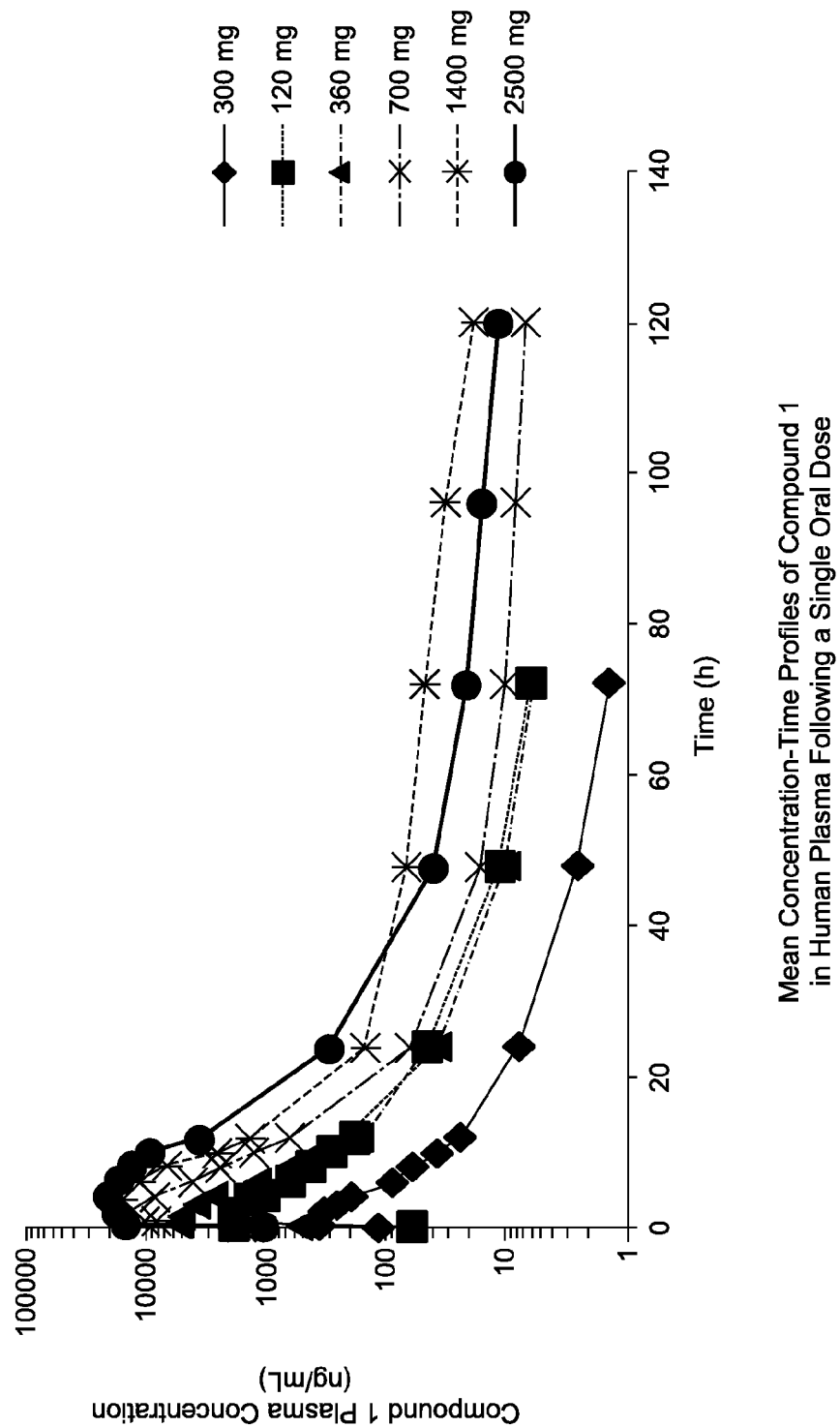
FIG. 5 depicts a line graph showing the mean concentration-time profiles of a compound N-(4-(4-(cyclopropylmethyl)piperazine-1-carbonyl)phenyl)quinoline-8-sulfonamide (Compound 1) in human plasma following a single oral dose at 30 mg, 120 mg, 360 mg, 700 mg, 1400 mg, and 2500 mg.
Figure 7:
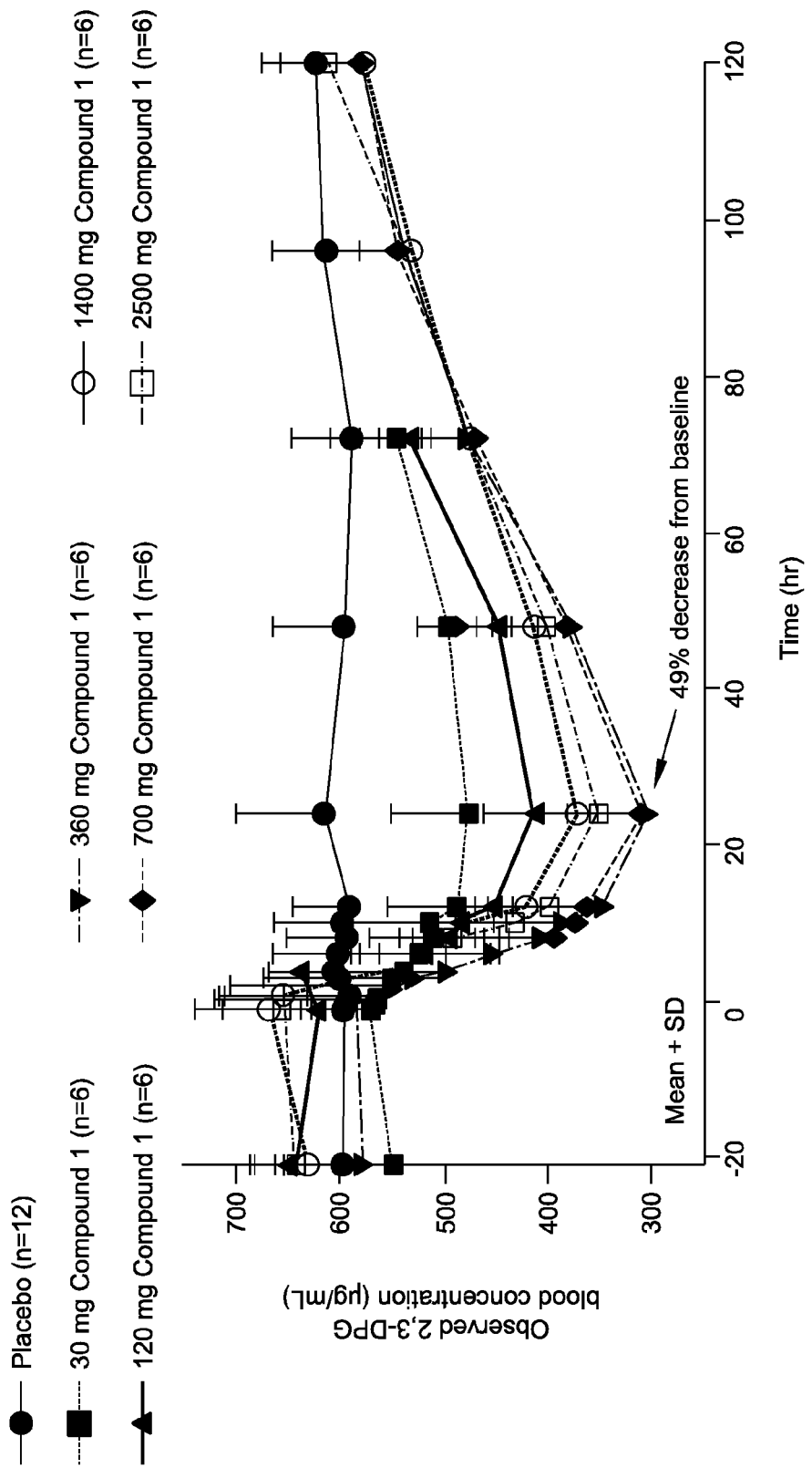
FIG. 7 depicts a line graph showing the mean concentration-time profiles of 2,3-DPG in human blood following a single oral dose of placebo, 30 mg, 120 mg, 360 mg, 700 mg, 1400 mg, and 2500 mg of a compound N-(4-(4-(cyclopropylmethyl)piperazine-1-carbonyl)phenyl)quinoline-8-sulfonamide (Compound 1).

In the SAD, all 48 subjects enrolled completed the study, which included 47 males and 1 female. These subjects represented a diverse racial and ethnic pool (15 White, 31 Black, 1 Asian, 1 Native Hawaiin or other Pacific Islander, wherein 7 subjects identify as Hispanic or Latino) and the mean age was about 40 years. Analysis of safety data indicated that 19/48 (39%) subjects receiving Compound 1 or placebo (P) under fasted and/or fed conditions experienced at least 1 treatment emergent adverse event (AE) during the study (FIG. 4). All AEs were mild or moderate (Grade 1 and 2) in severity, and the most common were nausea (n=5; 10%) and headache (n=8; 17%). In the 2 completed MAD cohorts (13 males; 3 females; mean age 44 years) 8/16 (50%) of subjects receiving Compound 1 or placebo experienced 11 AEs. All AEs were mild (n=10) or moderate (n=1) and the most frequent were venipuncture bruises. There were no serious AEs, discontinuations due to AEs, or dose-limiting toxicities in either study. Maximum tolerated dose was not reached in the SAD and dose escalation continues in the MAD. In SAD cohorts 1-6, exposure to single doses of Compound 1 increased in a dose-proportional manner (mean plasma $C_{max}$, $AUC_{0-12\ hr}$ and $AUC_{0-72\ hr}$) (FIG. 5). Absorption was rapid, with a median $T_{max}$ of 0.75-4.0 h. The pharmacokinetic parameter values of Compound 1 for each SAD cohort are summarized in FIG. 6. As expected, Compound 1 had a rapid distribution or elimination phase during the first 12 hours following dosing, with an apparent half-life of approximately 2-4 hours (FIG. 5). The mean apparent terminal half-life ($t_{1/2}$) ranged from 17.5-20.5 hours or 50-80 hours, when concentrations were measured for 72 or 120 hours, respectively (FIG. 6). In addition, a dose-dependent decrease in the concentration of the pharmacodynamic marker 2,3-DPG was observed over 24 hours following exposure to Compound 1 (with a 48% decrease), which returned to placebo levels after 72 hours (FIG. 7). Preliminary results indicated that food has a minimal effect on the exposure to Compound 1.

Multiple Ascending Dose (MAD) Study

Figure 8:
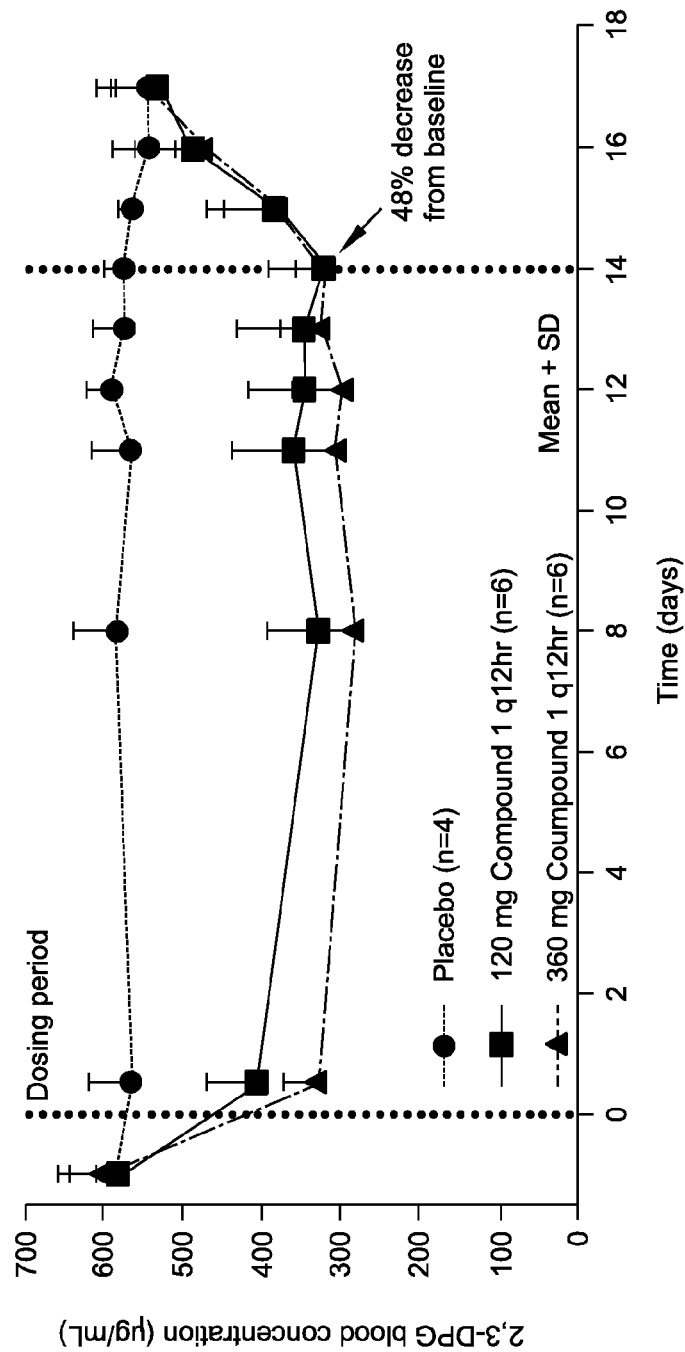
FIG. 8 depicts a line graph showing the mean blood concentration-time profiles of 2,3-DPG following multiple oral doses of placebo, 120 mg, and 360 mg of a compound N-(4-(4-(cyclopropylmethyl)piperazine-1-carbonyl)phenyl)quinoline-8-sulfonamide (Compound 1) for cohorts 1 and 2 in the MAD study.
Figure 9:
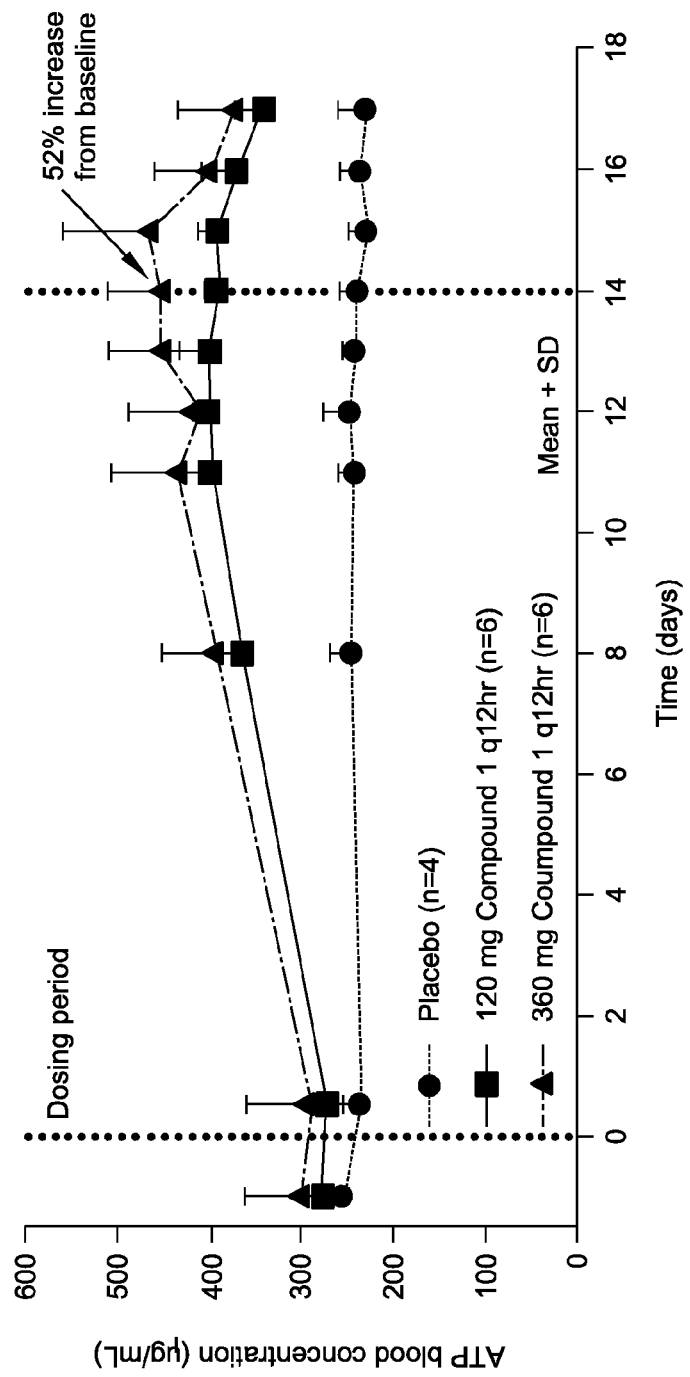
FIG. 9 depicts a line graph showing the mean blood concentration-time profiles of ATP following multiple oral doses of placebo, 120 mg, and 360 mg of a compound N-(4-(4-(cyclopropylmethyl)piperazine-1-carbonyl)phenyl)quinoline-8-sulfonamide (Compound 1) for cohorts 1 and 2 in the MAD study.

In the MAD study, the pharmacokinetic results for cohorts 1 and 2 on Day 1 were consistent with those of the SAD study. However, the pharmacokinetic parameter values of Compound 1 were lower on Day 14 compared with that on Day 1, suggesting that multiple doses of Compound 1 may result in an increase in the rate of drug metabolism. The decrease in exposure on Day 14 is consistent with pre-clinical data suggesting that Compound 1 is a moderate inducer of cytochrome P450 3A4 (CYP3A4), which is the major route of the oxidative metabolism of Compound 1. Similarly, decreases in 2,3-DPG levels were also observed after administration of the final dose in cohorts 1 and 2 of the MAD study. Concentrations of 2,3-DPG in the blood returned to placebo levels between 48 and 72 hours after the last dose (FIG. 8). There were minimal increases in blood ATP levels after a single dose of Compound 1 in the SAD study. In contrast, there were substantial increases in ATP levels in the blood on Days 8-14 of subjects in cohorts 1 and 2 in the MAD study, and levels remained elevated through 72 hours after the last dose (FIG. 9).

In the 6 sequential cohorts, 48 subjects (42 males and 6 females) with a mean age 41.5 (25-60) years were enrolled. Final, unblinded safety data showed ≥1 AE in 16 out of 36 (44%) subjects treated with Compound 1 and 4 out of the 12 (33%) placebo (P) subjects. Treatment related ≥1 AEs was noted in 11 out of the 36 (31%) subjects treated with Compound 1 and 3 out of the 12 (25%) placebo subjects. All treatment-related AEs were mild or moderate (only 1 grade 3 event) in severity and often reversible despite continued dosing. The most frequent Compound 1 related AEs were nausea and headache, 5 out of the 36 (14%) subjects for each (P: 0/12 (0%) nausea; headache 1 out of the 12 (8%)). Gastrointestinal AEs occurred in subjects treated with Compound 1 only at the highest dose, 700 mg q12h. One Grade 3 AE occurred (Compound 1 (700 mg q12h), elevated liver function tests (LFTs) which resolved after treatment discontinuation). There were four Compound 1 discontinuations: due to AEs in 2 subjects (Grade 2 drug eruption, 60 mg q12h; Grade 3 elevated LFTs, 700 mg q12h), and 2 subjects withdrew consent (both had Grade 1/2 nausea and Grade 1/1 vomiting, both at 700 mg q12h).

Figure 10A:
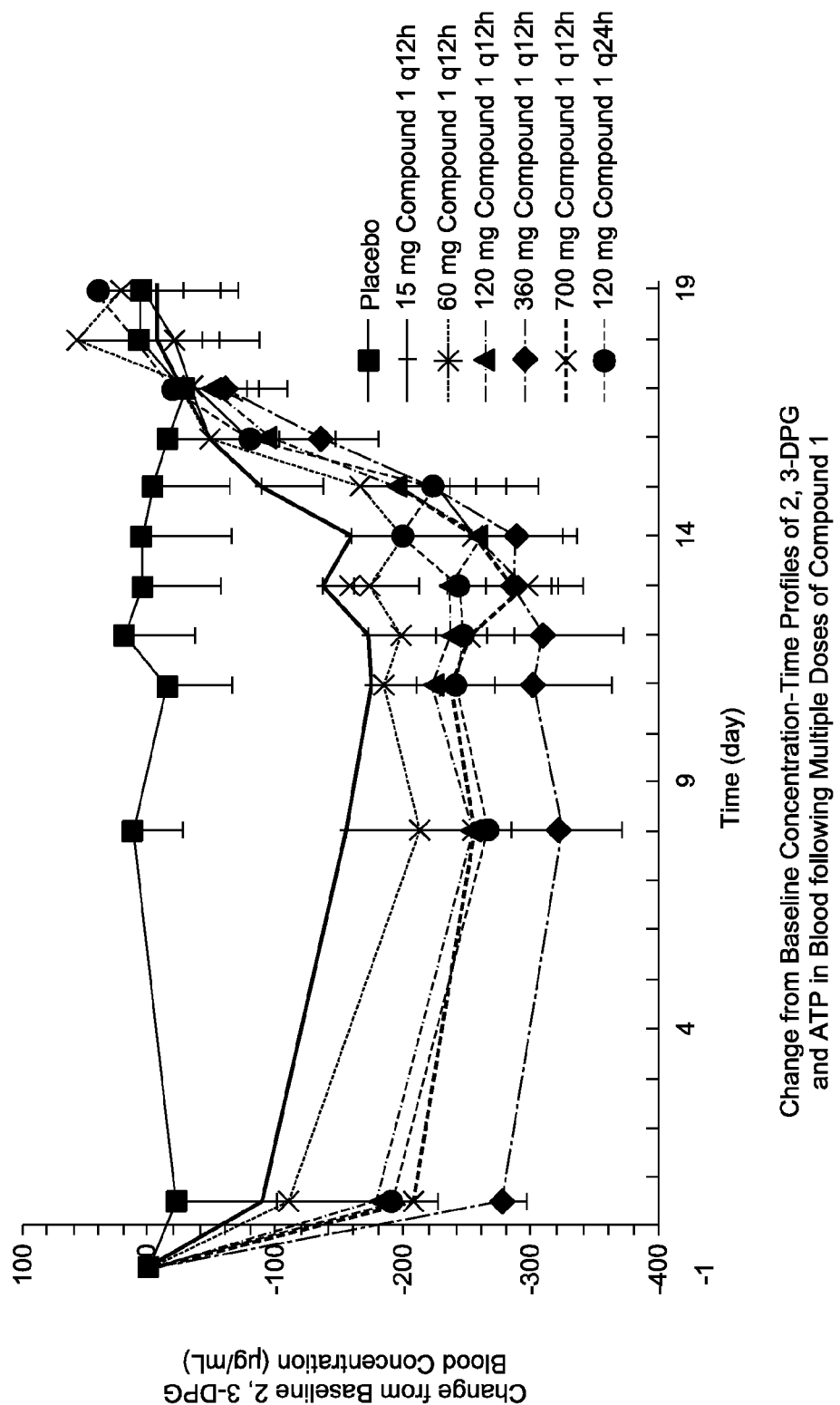
FIG. 10A depicts a line graph showing the change from baseline concentration-time profiles of 2,3-DPG following multiple oral doses of placebo, 15 mg (q12h), 60 mg (q12h), 120 mg (q12h), 360 mg (q12h), 700 mg (q12h) of a compound N-(4-(4-(cyclopropylmethyl)piperazine-1-carbonyl)phenyl)quinoline-8-sulfonamide (Compound 1), or a single dose of Compound 1 at 120 mg (q24h).
Figure 10B:
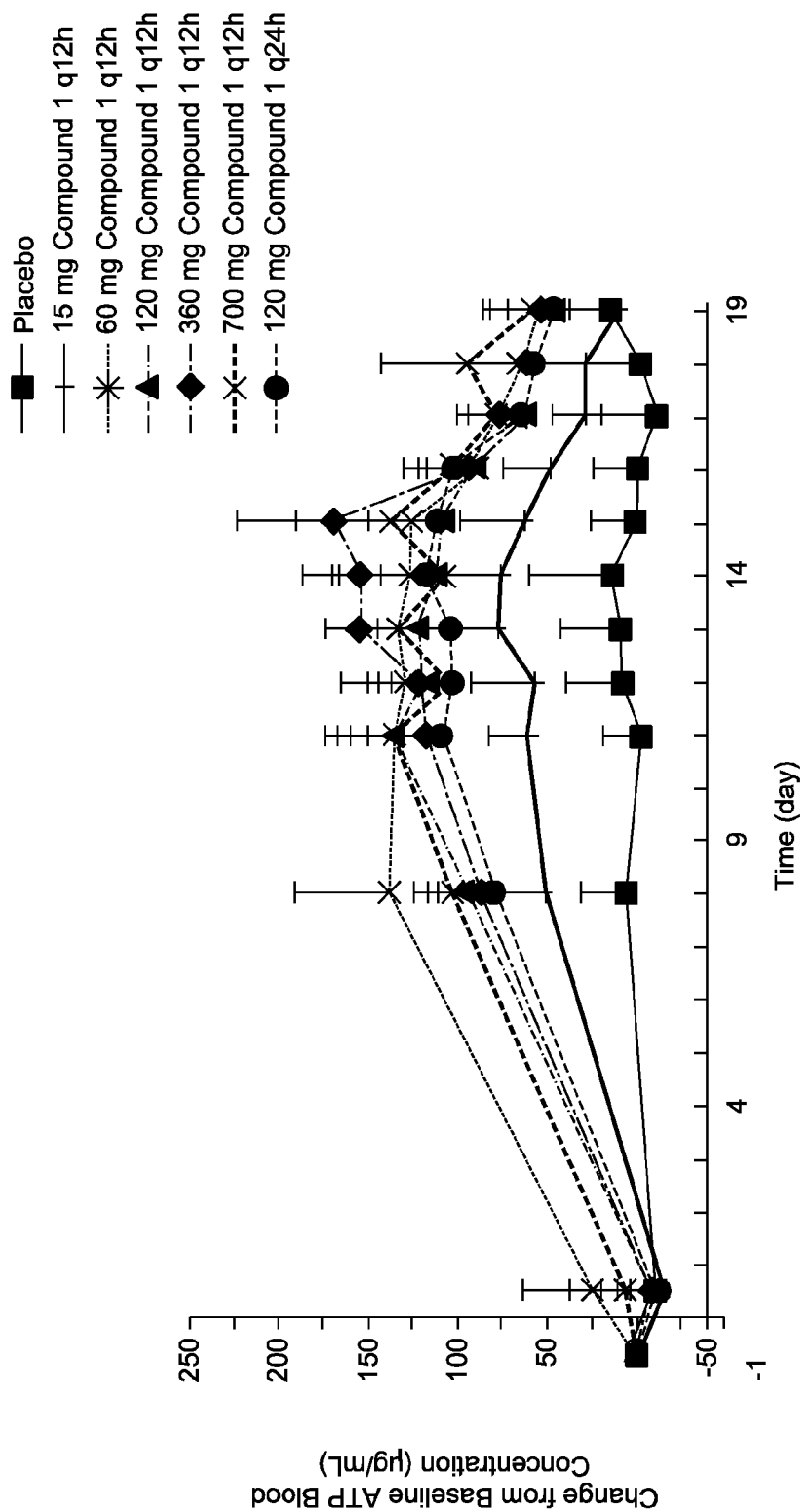
FIG. 10B depicts a line graph showing the change from baseline concentration-time profiles of ATP following multiple oral doses of placebo, 15 mg (q12h), 60 mg (q12h), 120 mg (q12h), 360 mg (q12h), 700 mg (q12h) of a compound N-(4-(4-(cyclopropylmethyl)piperazine-1-carbonyl)phenyl) quinoline-8-sulfonamide (Compound 1), or a single dose of Compound 1 at 120 mg (q24h).

The highest well-tolerated dose was 360 mg q12h (doses between 360 and 700 were not explored). Compound 1 plasma exposure was dose dependent with low to moderate variability in the PK parameters of Compound 1 and its metabolite. There was a dose-dependent decrease in 2,3-DPG and increase in ATP with the effects plateauing at 360 mg q12h. Decrease in 2,3-DPG was robust after Dose 1, while the increase in ATP occurred gradually and was strongly evident at Day 8. Change from baseline in 2,3-DPG and ATP plateaued at ~300 μg/ml (~50% decrease) and ~175 μg/ml (~50% increase), respectively (FIGS. 10A and 10B, respectively). After the final Day 14 dose, 2,3-DPG returned to levels similar to baseline between 72 and 120 hours (FIG. 10A). ATP levels remained elevated through 120 hours post-dose (FIG. 10B).

Compound 1 had a favorable safety profile and was well-tolerated in healthy subjects based on preliminary analysis of subjects receiving a single dose up to 2500 mg or multiple BID doses up to 360 mg for up to 14 days. Compound 1 also demonstrated a desirable PK profile, with rapid absorption, low PK variability and dose-proportional exposure with PD effect as demonstrated on 2,3-DPG and ATP. There were no serious AEs, discontinuations due to AEs, or dose-limiting toxicities in the SAD study, and so far no serious AEs in the MAD study.

The dose-dependent changes in ATP and 2,3-DPG blood levels seen in these studies are consistent with increased activity of the glycolytic pathway, which represents the expected pharmacodynamic effect of Compound 1. These data are consistent with pre-clinical studies in mice described in Example 2. As Compound 1 has roughly equipotent biochemical activity against wild type and mutant PKR enzymes, the data support the hypothesis that Compound 1 may be able to enhance glycolytic activity in red blood cells of patients with PKD to address the underlying cause of the diseases.

As shown in FIG. 10A there was a decrease in 2,3-DPG in blood with Compound 1. Mean 2,3-DPG blood levels generally decreased from baseline over the 12-hour post-dose period following the first dose of Compound 1 across the dose levels studied. The rate of decrease in 2,3-DPG levels was slower at lower doses. A large fraction of the decrease occurred after the first dose and the decrease reached its full extent within 7 days of dosing. Dose-related decreases in 2,3-DPG levels were observed with increasing doses of Compound 1 at low doses of 15 and 60 mg of Compound 1 q12h and reached a plateau over the 120 to 700 mg q12h dose levels, with minimal additional decreases with higher doses. The maximum decrease in 2,3-DPG levels was approximately 300 μg/mL, an approximately 50% decrease. The concentration of 2,3-DPG returned to baseline within 72 hours after the final dose of Compound 1.

As shown in FIG. 10B there was an increase in ATP in blood with Compound 1. ATP levels increased during multiple dose administration of Compound 1. Any effect of Compound 1 on ATP levels during the 12 hours following the first dose was minimal. The increase in ATP levels reached its full extent within 10 days of dosing. Increases in ATP levels were observed with increasing AG-348 doses at low doses of 15 and 60 mg AG-348 q12h and reached a plateau over the 120 to 700 mg dose levels, with minimal additional increases with higher doses. The maximum increase in ATP levels was approximately 175 μg/mL, an approximately 50% increase. The concentration of ATP remained elevated for 120 hours after the final dose of Compound 1.

Example 4. Clinical Studies of the Safety, Efficacy, Pharmacokinetics (PK), and Pharmacodynamics (PD) of a Pyruvate Kinase-R (PKR) Activator in Subjects with Pyruvate Kinase Deficiency This example describes a Phase 2, open-label, two-arm, multicenter, randomized, dose-ranging study of Compound 1 in adult patients with pyruvate kinase deficiency (PK deficiency). This is the first study to be conducted in patients with PK deficiency. The key objective of this study is to evaluate the safety and tolerability of up to 24 weeks of Compound 1 administration in patients with PK deficiency.

Methods

In this Phase 2, open label, two arm, multicenter, randomized, dose-ranging study, adult (male and female) patients with pyruvate kinase deficiency receive multiple doses of Compound 1 for up to 24 weeks. Pyruvate kinase deficiency in patients is confirmed by red blood cell (RBC) pyruvate kinase enzymatic assay. At Week 25, patients who safely tolerate Compound 1 and demonstrate clinical activity of Compound 1 may be eligible to roll over to a separate safety extension study for continued treatment. Patients who finish treatment at the end of 24 weeks or sooner will undergo follow-up assessment 4 weeks after the last dose of the study drug. Patients with toxicity suspected to be related to study drug will continue follow-up until the adverse event (AE) resolves, is declared chronic, or the patient is lost to follow-up.

Patient Selection

Patients are screened prior to randomization and Day 1 of the treatment period to meet certain criteria. Patients included in the study are adults (e.g., aged 18 or older) who have a medical history/diagnosis of pyruvate kinase deficiency and who are anemic but non-transfusion dependent.

Randomization and Dosing

Figure 11:
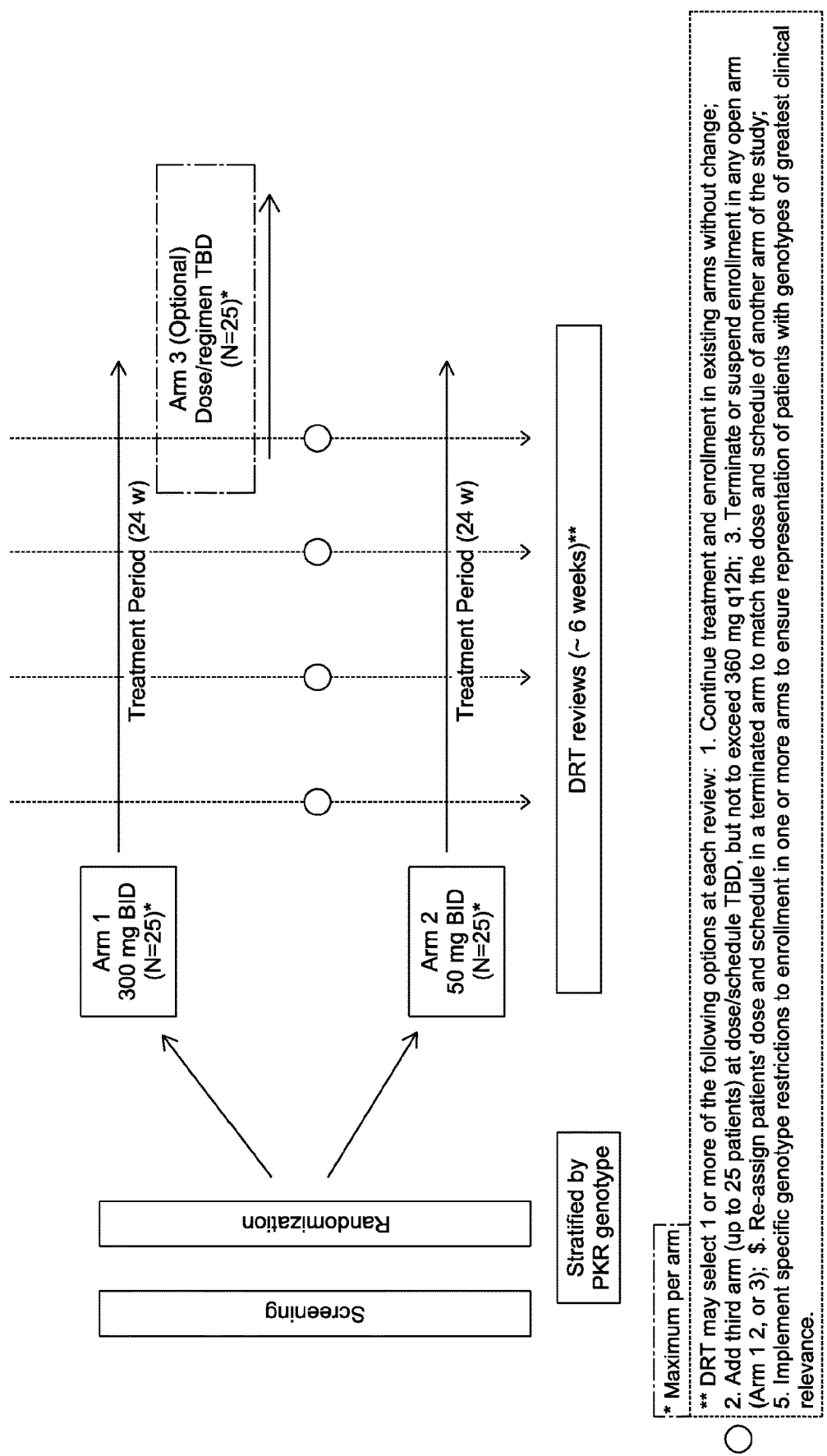
FIG. 11 is a schematic illustrating the Phase 2 study described in the Examples herein. BID (q12h)=twice-daily (every 12 hours); DRT=data review team; PKR=pyruvate kinase red blood cell isoform; TBD=to be determined; w=weeks.

Initially, up to 25 patients are randomized on an open-label, 1:1 basis to each of two arms, e.g., 25 patients per arm. In Arm 1, two twice-daily (BID) doses of Compound 1 are given—300 mg Compound 1 administered orally every 12 hours (q12h) (BID), e.g., with a minimum of 10 hours between doses. In Arm 2, 50 mg of Compound 1 is administered orally q12h (BID). (See FIG. 11) Starting with Day 1, dosing is continuous (e.g., there are no rest periods). Compound 1 is provided as a 25 mg or 100 mg (free-base equivalent) capsule of Compound 1. The number of capsules per dose will vary by assigned dose group. Patients will receive multiple oral (PO) doses of Compound 1 over a 24-week treatment period.

Patient Assessments

Safety will be monitored on an on-going basis, e.g., at regular intervals, or ad hoc as necessary. For example, adverse events (AEs), vital signs (VS), clinical laboratory (hematology, clinical chemistry, coagulation, and urinalysis), and electrocardiograms (ECGs) on enrolled patients are monitored. Additionally, available PK/PD data and indicators of clinical activity (e.g., changes from baseline in hemoglobin (Hb)) are assessed.

Pharmacokinetic and Pharmacodynamic Assessments

Pharmacokinetic assessments include serial blood sampling for determination of concentration-time profiles of Compound 1 and are conducted, e.g., following the first dose and the morning Day 15 dose. For example, additional trough levels of Compound 1 are obtained. Compound 1 is analyzed using assays to determine concentrations in plasma. Pharmacokinetic parameters on Day 1 and Day 15 are computed using standard non-compartmental methods based on observed plasma Compound 1 concentrations.

Pharmacodynamic assessments include serial blood sampling for determination of levels of ATP and 2,3-DPG. Serial blood sampling for determination of levels of ATP and, 2,3-DPG is conducted, e.g., following the first dose and the morning Day 15 dose, and additional trough levels of ATP and 2,3-DPG will be obtained. ATP and 2,3-DPG are analyzed using assays to determine concentrations in whole blood. Pharmacodynamic parameters on Day 1 and Day 15 are computed based on observed whole blood ATP and 2,3-DPG concentrations.

Figure 12:
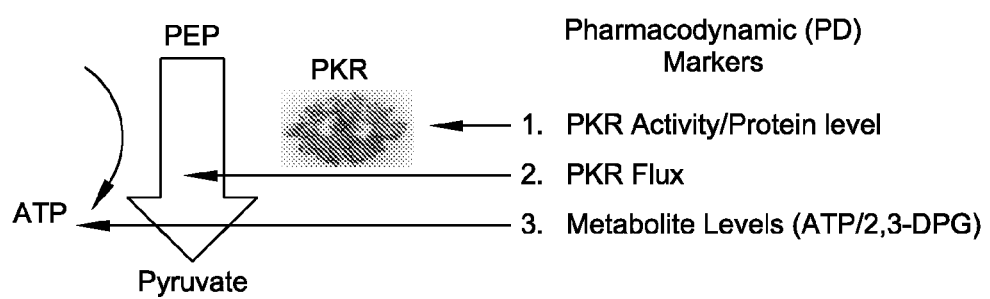
FIG. 12 is a schematic outlining the pyruvate kinase R (PKR) enzymatic reaction and how several pharmacodynamic (PD) assessments contributes to a mechanistic understanding of the action of Compound 1.

In some cases, assessments include determination of PKR activity, PKR protein, and glycolytic flux assays. Blood samples are evaluated for PKR activity in RBCs, and assessment of glycolytic flux in whole blood is performed through ex-vivo labeling with $^{13}C$-glucose. Blood is also evaluated for total PKR protein levels. Levels of additional metabolites are also assessed in blood samples to further elucidate the mechanism and effects of PKR activation by Compound 1. Exemplary PD markers are shown in FIG. 12. The PKR enzyme catalyzes the PEP-to-pyruvate reaction, with concomitant formation of ATP. Binding of Compound 1 to the PKR tetramer can be assessed through an ex-vivo biochemical assay of cell lysates from Compound 1 treated patients. PKR protein levels in whole blood are assessed through Western blotting or quantitative ELISA (or other similar assay).

The PKR Flux assay measures the change in carbon flow from glucose through the PKR reaction to pyruvate after Compound 1 treatment. This is distinct from the target engagement measured by the PKR activity assay because it is conducted in intact cells and thus a more direct and functional measure of pathway activity. The PKR Flux assay is performed by incubating freshly drawn patient blood at 37 degrees C. with $^{13}C6$-labeled glucose. Aliquots from the incubation reaction are taken over time and flash frozen. Subsequent analysis by mass spectrometry reveals the rate of label incorporation into glycolytic intermediates including DHAP, 2,3-DPG, 3-PG, and PEP. The data are fitted by mathematical modeling to quantitate the carbon flow through the PKR reaction. An increase in carbon flow through the PKR reaction indicates efficacy of Compound 1. Compound 1 target engagement and stimulation of glycolytic pathway activity has been shown in preclinical models and healthy volunteer clinical studies to result in accumulation of ATP and depletion of the upstream metabolite 2,3-DPG. Therefore, an increase in ATP levels and/or a decrease in 2,3-DPG levels indicates efficacy of Compound 1. Levels of these metabolites can be measured by mass spectrometry from frozen whole blood samples.

In some cases, exposure-response analysis is performed to evaluate the relationship of Compound 1 exposure and PD effects with changes in indicators of clinical activity (e.g., changes in Hb levels).

Additional or alternative data/observations other than those listed above may be reviewed. Based on the reviews, one or more of the following steps may be implemented:

Add 1 new dose arm (Arm 3) to enroll up to 25 patients at a dose to be determined; the dose for Arm 3 may be lower or higher than Arm 1 and Arm 2 doses, but will not exceed 360 mg q12h; and the dose regimen may be less frequent than q12h.

Having thus described several aspects of several embodiments, it is to be appreciated various alterations, modifications, and improvements will readily occur to those skilled in the art. Such alterations, modifications, and improvements are intended to be part of this invention, and are intended to be within the spirit and scope of the invention. Accordingly, the foregoing description and drawings are by way of example only.

We claim:

1. A method for treating pyruvate kinase deficiency (PKD) in a subject in need thereof, comprising orally administering to the subject once or twice daily a dose of about 10 mg to about 60 mg or about 60 mg to about 200 mg of (1) Compound 1 or a pharmaceutically acceptable salt or hydrate thereof; or (2) a pharmaceutical composition comprising Compound 1 or a pharmaceutically acceptable salt or hydrate thereof, and a pharmaceutically acceptable carrier, to thereby treat PKD in the subject, wherein Compound 1 is N-(4-(4-(cyclopropylmethyl)piperazine-1-carbonyl)phenyl)quinoline-8-sulfonamide.

2. The method of claim 1, wherein the method comprises orally administering to the subject once or twice daily a dose of about 10 mg to about 60 mg of Compound 1.

3. The method of claim 1, wherein the method comprises orally administering to the subject once or twice daily a dose of about 30 mg or about 120 mg of Compound 1.

4. The method of claim 1, wherein the method comprises orally administering to the subject once or twice daily a dose of about 60 mg to about 200 mg of Compound 1.

5. The method of claim 1, wherein the method comprises orally administering to the subject once or twice daily a dose of about 50 mg, about 75 mg, about 100 mg, about 125 mg, about 150 mg, about 175 mg or about 200 mg of Compound 1.

6. The method of claim 1, wherein the method comprises administering Compound 1 once daily.

7. A method for treating pyruvate kinase deficiency (PKD) in a subject in need thereof, comprising orally administering to the subject once or twice daily a dose of about 50 mg to about 300 mg of (1) Compound 1 or a pharmaceutically acceptable salt or hydrate thereof; or (2) a pharmaceutical composition comprising Compound 1 or a pharmaceutically acceptable salt or hydrate thereof, and a pharmaceutically acceptable carrier, to thereby treat PKD in the subject, wherein Compound 1 is N-(4-(4-(cyclopropylmethyl)piperazine-1-carbonyl)phenyl)quinoline-8-sulfonamide.

8. The method of claim 7 wherein the method comprises orally administering to the subject once or twice daily a dose of about 225 mg, about 250 mg, about 275 mg or about 300 mg of Compound 1.

9. The method of claim 1 wherein the method comprises administering Compound 1 twice daily.

10. The method of claim 1 wherein the method comprises administering twice daily a dose of about 50 mg of Compound 1.

11. The method of claim 1 wherein the method comprises administering twice daily a dose of about 100 mg of Compound 1.

12. The method of claim 1 wherein the method comprises administering Compound 1 at a dose of about 15 mg about every 12 hours, about 60 mg about every 12 hours, about 120 mg about every 12 hours.

13. The method of claim 1 wherein the method comprises administering Compound 1 at a dose of about 10 mg to about 60 mg about every 12 hours or about 60 mg to about 200 mg about every 12 hours.

14. The method of claim 1 wherein the method comprises administering Compound 1 at a dose of about 10 mg to about 60 mg about every 12 hours or about 60 mg to about 200 mg about every 12 hours.

15. The method of claim 1 wherein the method comprises administering Compound 1 at a dose of about 60 mg to about 200 mg about every 24 hours.

16. The method of claim 1 wherein the method comprises administering Compound 1 at a dose of about 90 mg about every 24 hours, about 120 mg about every 24 hours, about 150 mg about every 24 hours, about 180 mg about every 24 hours, or about 200 mg about every 24 hours.

* * * * *